(12) United States Patent
Kobayashi et al.

(10) Patent No.: US 6,245,843 B1
(45) Date of Patent: Jun. 12, 2001

(54) DIACETAL COMPOSITION, PROCESS FOR THE PREPARATION OF THE SAME, NUCLEATING AGENT FOR POLYOLEFINS CONTAINING THE SAME, POLYOLEFIN RESIN COMPOSITIONS, AND MOLDINGS

(75) Inventors: Toshiaki Kobayashi, Nara; Masahide Ishikawa, Uji; Harutomo Nomoto, Kyoto; Toshihiro Mizutani, Nara, all of (JP)

(73) Assignee: New Japan Chemical Co., Ltd. (JP)

( * ) Notice: Subject to any disclaimer, the term of this patent is extended or adjusted under 35 U.S.C. 154(b) by 0 days.

(21) Appl. No.: 09/319,187

(22) PCT Filed: Jul. 7, 1998

(86) PCT No.: PCT/JP98/03046

§ 371 Date: Jun. 2, 1999

§ 102(e) Date: Jun. 2, 1999

(87) PCT Pub. No.: WO99/18108

PCT Pub. Date: Apr. 15, 1999

(30) Foreign Application Priority Data

Oct. 3, 1997 (JP) .................................................. 10-287924
Mar. 4, 1998 (JP) .................................................. 10-071362
Apr. 2, 1998 (JP) .................................................. 10-090173

(51) Int. Cl.$^7$ ........................................................ C08K 5/15
(52) U.S. Cl. ............................................................ 524/109
(58) Field of Search ............................................ 524/109

(56) References Cited

U.S. PATENT DOCUMENTS 4,388,119    6/1983   Uchiyama .
4,611,024 *  9/1986   Wolfe ................................. 524/366
6,043,303 *  3/2000   Kobayashi ......................... 524/109

FOREIGN PATENT DOCUMENTS

| 64-413 | 1/1989 | (JP) . |
|---|---|---|
| 1-126352 | 5/1989 | (JP) . |
| 3-68579 | 3/1991 | (JP) . |
| 4-82890 | 3/1992 | (JP) . |
| 8-27323 | 1/1996 | (JP) . |
| 8-245843 | 9/1996 | (JP) . |

* cited by examiner

Primary Examiner—Paul R. Michl
(74) Attorney, Agent, or Firm—Larson & Taylor, PLC

(57) ABSTRACT

This invention provides a granular or powdery diacetal composition comprising:

(a) at least one diacetal such as 1,3:2,4-O-dibenzylidene-D-sorbitol or a nucleus-substituted derivative thereof, and (b) at least one binder selected from the group consisting of neutral or weakly acidic monovalent organic acids, neutral or weakly acidic polyvalent organic acids, partial salts of neutral or weakly acidic polyvalent organic acids, salts of sulfuric acid ester, sulfonic acid salts, salts of phosphoric acid ester, phosphoric acid esters, phosphorous acid esters and aluminum salts of a neutral or weakly acidic monovalent organic acid, the binder being uniformly dispersed on the surface and in the interior of the particles of the granular or powdery diacetal composition; a process for preparing the composition; a polyolefin resin nucleating agent comprising the composition; a resin composition containing the nucleating agent and a polyolefin resin; and a polyolefin resin molded article.

43 Claims, No Drawings

DIACETAL COMPOSITION, PROCESS FOR THE PREPARATION OF THE SAME, NUCLEATING AGENT FOR POLYOLEFINS CONTAINING THE SAME, POLYOLEFIN RESIN COMPOSITIONS, AND MOLDINGS

TECHNICAL FIELD

The present invention relates to a diacetal composition. More specifically, the invention relates to a diacetal composition which is in the form of a powder or in the form of granulated product and which comprises a powdery diacetal and a binder containing at least one member of organic acids and derivatives thereof serving as melting point depressing agents, the binder being uniformly dispersed in the diacetal particles; and a process for preparing said composition.

The present invention also relates to a polyolefin resin nucleating agent containing said powdery diacetal composition or said diacetal composition in the form of granulated product; polyolefin resin compositions and molded articles prepared from said nucleating agent and a polyolefin resin; and a process for molding said polyolefin resin compositions.

BACKGROUND ART

Diacetals such as dibenzylidene sorbitols and nucleus-substituted dibenzylidene sorbitols are widely used as nucleating agents for polyolefin resins, gelling agents for various fluids, etc. For use as these agents, diacetals need to be dissolved or to be dispersed by molecular order in molten polyolefin resins or fluids.

However, particles of diacetal powders have strong self-agglomeration properties and a high melting point, so that it is not easy to uniformly dissolve or disperse them for industrial purposes. Therefore, some measures must be taken to improve the solubility and dispersibility of diacetals.

A known process for improving the solubility and dispersibility of diacetals comprises treating a diacetal at a temperature equal to or higher than its melting point or melting temperature. However, diacetals, when treated at a high temperature for a long period, undergo heat decomposition or cause coloration, failing to fully exhibit their properties. Thus, the process has problems with functions of diacetals, and is disadvantageous in respect of energy saving.

Japanese Unexamined Patent Publication No. 145431/1994 discloses a process comprising reducing a diacetal to an ultrafine powder to improve the dispersibility and solubility. The ultrafine size powder of solid diacetals, however, deteriorates the working environment since it generates dust which may explode or influence the human body by inhalation thereof. Further, the ultrafine diacetal powder is likely to agglomerate again during storage, and are lower in workabilities such as flow property and transferability (easiness of transferring diacetal powders through piping). Thus, this technique causes industrially serious problems. Moreover, the disclosed technique intends to render the particle size distribution almost monodisperse, thereby necessitating an expensive special milling apparatus.

Further known are processes for increasing the compatibility of a diacetal with polyolefin resins using an organic carboxylic acid in combination with the diacetal (Japanese Unexamined Patent Publication No. 122150/1976, Japanese Examined Patent Publication No. 413/1989 and Japanese Unexamined Patent Publication No. 101131/1985).

The process disclosed in Japanese Unexamined Patent Publication No. 122150/1976 comprises adding dibenzylidene sorbitol and an organic carboxylic acid separately and directly to a polyolefin resin to thereby increase the compatibility of dibenzylidene sorbitol with the resin. The process, however, does not depress the high melting point of the dibenzylidene sorbitol, insufficiently solving the problem of white hard spots formed from undissolved dibenzylidene sorbitol in the resin.

According to the processes of Japanese Examined Patent Publication No. 413/1989 and Japanese Unexamined Patent Publication No. 101131/1985, the surfaces of dibenzylidene sorbitol particles are coated in advance with a higher fatty acid or terephthalic acid, and the coated particles are added to a polyolefin resin. The coated dibenzylidene sorbitol particles have higher compatibility with molten resins than that of uncoated dibenzylidene sorbitol. However, these processes are also unsatisfactory, since the problem of white hard spots of undissolved matter still remains. Thus, the processes do not sufficiently improve the transparency of the resin, and the impaired appearance decreases the commercial value of the product. The same problem arises also when the diacetal particles are surface-coated with a higher fatty acid simply using an organic acid.

Further, a clarifying nucleating agent for polyolefin resins having improved moldability is proposed (Japanese Unexamined Patent Publication No. 245843/1996), which enables molding at a temperature lower than conventional molding temperatures (hereinafter referred to as "low-temperature molding"), the nucleating agent being prepared by mixing an aliphatic carboxylic acid amide and/or an aromatic carboxylic acid amide with a dibenzylidene sorbitol or coating the surfaces of dibenzylidene sorbitol particles with an aliphatic carboxylic acid amide and/or an aromatic carboxylic acid amide. However, said mixing process forms a hard gel when removing the solvent, and thus is difficult to employ for industrial purposes. Said coating process does not exhibit sufficient melting point depressing effect in spite of the large amount of the coating agent, i.e., aliphatic carboxylic acid amide and/or aromatic carboxylic acid amide. Moreover, said amide compounds tends to bleed from polyolefin resin molded articles, and therefore when the coating amount thereof is large, the resulting polyolefin resin molded article prepared from the diacetal coated with said coating agent and a polyolefin resin has problems such as lowered heat-sealing strength. Thus, said process still remains to be improved.

DISCLOSURE OF THE INVENTION

An object of the present invention is to provide a method for significantly improving the solubility and dispersibility of diacetals in various molten resins or various fluids, while increasing the flow property and transferability (easiness of transfer through piping, due to low friction among particles of the powder) of diacetals and suppressing dust generation and adhesion to walls of pipes, hoppers or other equipments.

Another object of the invention is to provide a composition which exhibits polyolefin resin nucleating properties in a low-temperature molding.

The present inventors carried out extensive research to achieve the above objects and found that, when a specific compound is uniformly dispersed in a diacetal swelled with a solvent and the uniform dispersion is dried and granulated or made into a powder, the following advantages can be obtained.

(1) The melting point of the diacetal is effectively and greatly depressed.

(2) The diacetal composition obtained by uniformly dispersing the specific compound in the particles of the diacetal powder is improved in solubility, dispersibility and dissolution rate in molten resins and various fluids, regardless of the shape of the composition.

(3) The binder effect (effect of promoting aggregation or agglomeration of the particles) of said specific compound makes it possible to adjust the bulk density of the diacetal composition to a desired value within the range of 0.2 g/cm$^3$ or more, thereby improving the flow property and transferability of the diacetal powder, suppressing generation of dust, and also suppressing adhesion of the diacetal to the walls of equipments such as pipes and hoppers.

(4) The diacetal composition, when used for forming pellets of a polyolefin resin, exhibits its inherent nucleating properties very easily, without staining the extrusion dies or molded articles due to the sublimation of the nucleating agent.

Generally, when a diacetal composition has an increased apparent density, it has an improved flow property of the powder but has a lowered dissolution rate. Conversely, when the apparent density of a diacetal is decreased, the dissolution rate is increased but the flow property of it is lowered. The present inventors succeeded in significantly lowering the melting point of a diacetal composition, and this success solved the problem of improving the flow property of the powder due to an increased apparent density and the problem of improving the dissolution rate at the same time.

The present invention has been accomplished based on these novel findings.

The present invention provides a granular or powdery diacetal composition comprising:

(a) at least one diacetal represented by the formula (1)

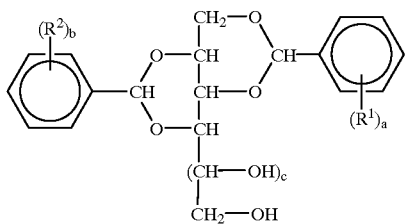

(1)

wherein $R^1$ and $R^2$ are the same or different and each represent a hydrogen atom, an alkyl group having 1 to 4 carbon atoms, an alkoxy group having 1 to 4 carbon atoms, an alkoxycarbonyl group having 1 to 4 carbon atoms or a halogen atom; a and b each represent an integer of 1 to 5; c represents 0 or 1; when a is 2, the two $R^1$ groups taken together with the benzene ring to which they are attached may form a tetralin ring; and when b is 2, the two $R^2$ groups taken together with the benzene ring to which they are bonded may form a tetralin ring; and (b) a binder containing at least one member selected from the group consisting of neutral or weakly acidic monovalent organic acids, neutral or weakly acidic polyvalent organic acids, partial salts of neutral or weakly acidic polyvalent organic acids, salts of strongly acidic organic acids (in particular, sulfuric acid ester salts, sulfonic acid salts and phosphoric acid ester salts), phosphoric acid esters, phosphorous acid esters and aluminum salts of neutral or weakly acidic monovalent organic acids; the binder being uniformly dispersed in the particles of the granular or powdery diacetal composition.

The above organic acid may have, in the molecule, one or more bonds other than the carbon-carbon bond (for example, an ether bond, an ester bond, a thioether bond, an amide bond, etc.) and/or one or more functional groups (for example, halogen atom, amino group, hydroxyl group, heterocyclic group, carbonyl group, etc). Further, in the neutral or weakly acidic organic acid with a valency of two or more (i.e., organic acid having two or more monovalent acid groups in the molecule), part of the acid moieties may form a salt with an alkali metal (such as lithium, potassium, sodium, etc.), an alkaline earth metal (such as calcium, etc.), an amine (e.g., tri($C_1$–$C_4$ alkyl)amine such as triethylamine, trimethylamine, etc.), ammonium or the like. The strongly acidic organic acid is usually used in the form of a salt (i.e., in the form of a neutral, weakly acidic or weakly basic salt). The aluminum salts are salts of one, two or three molecules of a monovalent organic acid with one atom of aluminum.

The diacetal composition of the invention is generally in the form of a powder or granule. Preferably, it is in the form of a powder with an average particle diameter of 3 to 2000 μm, or in the form of a granulated product or a molded product having a shape of cylinders or the like.

The present invention has been accomplished based on the unexpected findings that the melting point of the diacetal composition is (1) depressed with an increasing degree of swelling of the diacetal during the preparation of the composition, (2) greatly depressed as compared with that of the merely surface-coated diacetals, and (3) remarkably depressed when the specific compound is used. The degree of swelling depends on the degree of mixing with heating in a solvent to be described later in detail. In particular, the degree of swelling is increased by mixing with heating in the presence of a polar organic solvent, as will be described later.

The diacetal composition of the invention is prepared, as will be described hereinafter, by uniformly mixing the above binder and a diacetal sufficiently swelled with a solvent (such as alcohol or water), and making the obtained swelled diacetal composition into a powder while drying the swelled composition or granulating the swelled composition while drying it.

Solid diacetals are composed of aggregates of numerous diacetal fibrous crystals. In the diacetal swelled with a solvent such as water or an organic solvent, the solvent has permeated into the interspaces among numerous fibrous crystals which aggregated as a solid, and the entanglement of fibrous crystals comes loose and the degree of aggregation becomes poorer so that the apparent volume thereof is increased. When the swelled diacetal is uniformly mixed with the binder, the binder permeates into the interspaces among the fibrous crystals of the diacetal and is uniformly dispersed by molecular order.

Subsequently, said uniformly dispersed product is made into a powder or granules, by granulating the product with drying, or by drying said uniformly dispersed product and pulverizing the dried product, or by granulating the powder obtained after pulverizing the dried product, or by pulverizing the granulated product, thereby giving a composition wherein the binder is uniformly distributed among the diacetal fibrous crystals (hereinafter referred to simply as "diacetal composition").

As a result, the granular or powdery diacetal composition of the invention comprises the binder uniformly distributed not only on the surfaces of the diacetal particles but also within the diacetal particles. That is, the binder is uniformly dispersed among the diacetal fibrous crystals constituting the diacetal particles.

Accordingly, the diacetal composition of the invention is fundamentally different, in the binder concentration distribution and degree of melting point depression, from the diacetal disclosed in Japanese Unexamined Patent Publication No. 245843/1996 which is prepared by simply mixing the diacetal with a carboxylic acid amide without swelling the diacetal particles with a solvent, or by surface-coating diacetal particles with a carboxylic acid amide.

The present invention also provides a process for preparing said diacetal composition.

The present invention further provides a polyolefin resin nucleating agent containing said diacetal composition.

The present invention also provides polyolefin resin compositions or pellets prepared from said nucleating agent and a polyolefin resin, and molded articles obtained by molding the polyolefin resin composition.

Moreover, the present invention provides a process for molding the polyolefin resin composition.

According to one embodiment of the present invention, a powdery uniformly dispersed diacetal composition (namely, a composition in which the binder is uniformly dispersed in the diacetal) is provided which comprises (a) at least one diacetal represented by the formula (1) wherein $R^1$ and $R^2$ are the same or different and each represent a hydrogen atom, an alkyl group having 1 to 4 carbon atoms, an alkoxy group having 1 to 4 carbon atoms, an alkoxycarbonyl group having 1 to 4 carbon atoms or a halogen atom, a and b each represent an integer of 1 to 5 and c represents 0 or 1, and (b) a binder comprising at least one organic acid as an essential component, the diacetal composition having an average particle diameter of 3 to 500 µm.

In the above embodiment, the organic acid is preferably a compound which can depress the melting point of the diacetal by 7° C. or more when 10 wt. parts of the organic acid is uniformly dispersed in 90 wt. parts of the diacetal.

In the above embodiment, the bulk density of said composition is preferably 0.2 to 0.9 g/cm³. A preferred acid value of the organic acid is 60 to 1200 mg KOH/g.

According to the above embodiment, a nucleating agent for polyolefin is also provided which contains said diacetal composition.

The present invention will be described below in detail.

Diacetal

As to $R^1$ and $R^2$ in the above formula (1), the alkyl group having 1 to 4 carbon atoms includes methyl, ethyl, propyl, isopropyl, butyl, etc., the alkoxy group having 1 to 4 carbon atoms includes methoxy, ethoxy, propoxy, isopropoxy, butoxy, etc., and the alkoxycarbonyl groups having 1 to 4 carbon atoms includes methoxycarbonyl, ethoxycarobonyl, propoxycarbonyl and isopropoxycarbonyl, and the halogen atom includes fluorine, chlorine and bromine.

a and b each represents an integer of 1 to 5, preferably 1, 2 or 3. c is preferably 1. The position(s) of the substituents represented by $R^1$ and $R^2$ is(are) not limited and may be, for example, o-, m- or p-position when a and b each represent 1, and may be, for example, 2,4-, 3,4- or 3,5-positions when a and b each represent 2, or may be, for example, 2,4,5- or 3,4,5-positions when a and b each represent 3.

All of the diacetals represented by the formula (1) are known or readily prepared by known processes, for example, those described in Japanese Examined Patent Publication No. 43748/1973 and Japanese Unexamined Patent Publications Nos. 5165/1978, 185287/1982 and 231488/1990.

The following are typical examples of the diacetal represented by the formula (1):

1,3:2,4-O-dibenzylidene-D-sorbitol,
1,3:2,4-bis-O-(m-methylbenzylidene)-D-sorbitol,
1,3:2,4-bis-O-(m-ethylbenzylidene)-D-sorbitol,
1,3:2,4-bis-O-(m-isopropylbenzylidene)-D-sorbitol,
1,3:2,4-bis-O-(m-n-propylbenzylidene)-D-sorbitol,
1,3:2,4-bis-O-(m-n-butylbenzylidene)-D-sorbitol,
1,3:2,4-bis-O-(p-methylbenzylidene)-D-sorbitol,
1,3:2,4-bis-O-(p-ethylbenzylidene)-D-sorbitol,
1,3:2,4-bis-O-(p-isopropylbenzylidene)-D-sorbitol,
1,3:2,4-bis-O-(p-n-propylbenzylidene)-D-sorbitol,
1,3:2,4-bis-O-(p-n-butylbenzylidene)-D-sorbitol,
1,3:2,4-bis-O-(2,3-dimethylbenzylidene)-D-sorbitol,
1,3:2,4-bis-O-(2,4-dimethylbenzylidene)-D-sorbitol,
1,3:2,4-bis-O-(2,5-dimethylbenzylidene)-D-sorbitol,
1,3:2,4-bis-O-(3,4-dimethylbenzylidene)-D-sorbitol,
1,3:2,4-bis-O-(3,5-dimethylbenzylidene)-D-sorbitol,
1,3:2,4-bis-O-(2,3-diethylbenzylidene)-D-sorbitol,
1,3:2,4-bis-O-(2,4-diethylbenzylidene)-D-sorbitol,
1,3:2,4-bis-O-(2,5-diethylbenzylidene)-D-sorbitol,
1,3:2,4-bis-O-(3,4-diethylbenzylidene)-D-sorbitol,
1,3:2,4-bis-O-(3,5-diethylbenzylidene)-D-sorbitol,
1,3:2,4-bis-O-(2,4,5-trimethylbenzylidene)-D-sorbitol,
1,3:2,4-bis-O-(3,4,5-trimethylbenzylidene)-D-sorbitol,
1,3:2,4-bis-O-(2,4,5-triethylbenzylidene)-D-sorbitol,
1,3:2,4-bis-O-(3,4,5-triethylbenzylidene)-D-sorbitol,
1,3:2,4-bis-O-(p-methyloxycarbonylbenzylidene)-D-sorbitol,
1,3:2,4-bis-O-(p-ethyloxycarbonylbenzylidene)-D-sorbitol,
1,3:2,4-bis-O-(p-isopropyloxycarbonylbenzylidene)-D-sorbitol,
1,3:2,4-bis-O-(o-n-propyloxycarbonylbenzylidene)-D-sorbitol,
1,3:2,4-bis-O-(o-n-butylbenzylidene)-D-sorbitol,
1,3:2,4-bis-O-(o-chlorobenzylidene)-D-sorbitol,
1,3:2,4-bis-O-(p-chlorobenzylidene)-D-sorbitol,
1,3:2,4-bis-O-[(5,6,7,8-tetrahydro-1-naphthalene)-1-methylene)]-D-sorbitol, 1,3:2,4-bis-O-[(5,6,7,8-tetrahydro-2-naphthalene)-1-methylene]-D-sorbitol,
1,3-O-benzylidene-2,4-O-p-methylbenzylidene-D-sorbitol,
1,3-O-p-methylbenzylidene-2,4-O-benzylidene-D-sorbitol,
1,3-O-benzylidene-2,4-O-p-ethylbenzylidene-D-sorbitol,
1,3-O-p-ethylbenzylidene-2,4-O-benzylidene-D-sorbitol,
1,3-O-benzylidene-2,4-O-p-chlorobenzylidene-D-sorbitol,
1,3-O-p-chlorobenzylidene-2,4-O-benzylidene-D-sorbitol,
1,3-O-benzylidene-2,4-O-(2,4-dimethylbenzylidene)-D-sorbitol,
1,3-O-(2,4-dimethylbenzylidene)-2,4-O-benzylidene-D-sorbitol,
1,3-O-benzylidene-2,4-O-(3,4-dimethylbenzylidene)-D-sorbitol,
1,3-O-(3,4-dimethylbenzylidene)-2,4-O-benzylidene-D-sorbitol, 1,3-O-p-methyl-benzylidene-2,4-O-p-ethylbenzylidene sorbitol, 1,3-p-ethyl-benzylidene-2,4-p-methylbenzylidene-D-sorbitol, 1,3-O-p-methyl-benzylidene-2,4-O-p-chlorobenzylidene-D-sorbitol, and 1,3-O-p-chloro-benzylidene-2,4-O-p-methylbenzylidene-D-sorbitol.

These diacetals can be used singly or at least two of them may be used in combination.

The crystal form of the diacetal is not limited insofar as the contemplated effects of the invention can be achieved, and may be hexagonal, monoclinic, cubic or other system. These crystals are known or can be prepared by known processes.

The starting diacetal to be used in the present invention may be one in which the purity of 1,3:2,4-compound represented by the formula (1) is 100%, but may be one containing a small amount of impurities. Generally, the starting diacetal may be one in which the purity of 1,3:2,4-compound represented by the formula (1) is at least 90 weight %, preferably at least 95 weight % and particularly preferably at least 97 weight %.

Diacetal compounds formed by the reaction of a pentahydric or hexahydric alcohol such as D-sorbitol and an optionally substituted aromatic aldehyde (in particular, optionally substituted benzaldehyde) as the starting materials for synthesizing the diacetal represented by the formula (1) include 1,3:2,4-diacetal represented by the formula (1) and additionally other acetal compounds (by-products), e.g., monoacetals such as 1,2-compound, 3,4-compound, 2,4-compound, 1,3-compound and the like, triacetals such as 1,3:2,4:5,6-compound, 1,2:3,4:5,6-compound and the like, and diacetal isomers such as 1,2:3,4-compound and the like. The diacetal composition of the present invention may contain, in addition to the diacetal represented by the formula (1), at least one species selected from the group consisting of monoacetals, triacetals and diacetal isomers, as impurities, and in such a case, the presence of such impurities in a total amount of not more than 10 wt. %, particularly 0.05–10 wt. %, preferably 0.1–5 wt. %, more preferably 0.1–3 wt. % or less, based on the total amount of the acetals (total amount of 1,3:2,4-diacetal represented by the formula (1), monoacetals, triacetals and isomers of the diacetal), do not cause any particular problems, but rather is beneficial from the standpoint of depressing the melting point of the diacetal composition of the present invention. However, the presence of said impurities in an amount of more than 10 wt. % tend to deteriorate the nucleating performance.

Binder

According to the invention, examples of the binder include neutral or weakly acidic monovalent organic acids, neutral or weakly acidic polyvalent organic acids, partial salts of neutral or weakly acidic polyvalent organic acids, and further include salts of strongly acidic organic acids such as sulfuric acid ester salts, sulfonic acid salts and phosphoric acid ester salts, and additionally include phosphoric acid esters, phosphorous acid esters and aluminum salts of neutral or weakly acidic monovalent organic acids. These may be used singly or at least two of them may be used in combination.

The binder according to the present invention, when uniformly dispersed in the diacetal by the process to be described hereinafter, efficiently depresses the melting point of the diacetal and increases the bulk density of the powder of the diacetal. These two effects greatly increase the solubility and dispersibility of the diacetal powder in molten resins or various fluids, and at the same time, improve the flow property and transferability of the diacetal composition in the form of a powder, granules or moldings, and suppress generation of dust and adhesion of the diacetal to walls of pipes, hoppers and other equipments.

As mentioned above, the diacetal composition of the invention has a melting point drastically lower than that of the diacetal which constitutes the composition. When the diacetal composition of the invention is added to a polyolefin resin for molding, the diacetal composition of the invention dissolves or disperses in a molten polyolefin resin at a temperature in the vicinity of the melting point of the diacetal composition. Accordingly, pellets of the polyolefin resin can be prepared by mixing the composition of the invention with the molten polyolefin resin at a resin temperature set to a vicinity of the melting point of the diacetal composition, and then cooling and cutting the mixture. That is, the extrusion molding can be carried out at a temperature significantly lower than the conventional molding temperature, making it unnecessary to reduce the nucleating agent to an ultrafine powder. Since the lower molding temperature prevents sublimation of the nucleating agent, the composition of the invention exhibits its nucleating properties very easily and improves the productivity of polyolefin resin pellets.

For the same reason, a powdery resin composition comprising a powdery resin, the diacetal composition of the invention and if desired resin additives can be directly subjected as such to a injection molding, extrusion molding, or the like, without making the resin composition into polyolefin resin pellets in advance. In such direct molding, the composition of the invention not only enables low-temperature molding but also suppresses the mold-stain and the stain of molded articles such as sheets caused by sublimation of the diacetal.

The binder is used, for example, in an amount of 0.01 to 100 wt. parts, preferably 0.1 to 70 wt. parts, more preferably 0.2 to 25 wt. parts, per 100 wt. parts of the diacetal represented by the formula (1). If the amount is less than 0.01 wt. part, both melting point depressing effect and binder effect are difficult to obtain. On the other hand, an amount exceeding 100 wt. parts brings no specific advantages in the melting point depressing effect or binder effect, and is likely to impair the transparency of resins when the composition of the invention is used as a nucleating agent. As will be described hereinafter, when a hydroxycarboxylic acid is used, as the binder, even in a very small amount, the melting point of the diacetal is remarkably depressed compared with the melting point of the diacetal per se.

Of the above-mentioned binders, recommended is the binder which depresses the melting point of the diacetal by 7° C. or more, preferably 20° C. or more, more preferably 40° C. or more, and still more preferably 90° C. or more, when the diacetal composition of the invention is prepared by uniformly dispersing 10 wt. parts of the binder in 90 wt. parts of the diacetal represented by the formula (1) according to the invention. It is also recommended that the melting point and/or softening point of the binder per se is not higher than the melting point of the diacetal in which the binder is uniformly dispersed. The above binders may be used singly or at least two of them may be used in admixture.

From the standpoint of the melting point depression, preferred are organic acids, in particular mono- or polycarboxylic acids, having an acid value of about 60 to 1200 mg KOH/g, and more preferred are organic acids, in particular mono- or polycarboxylic acids, having an acid value of about 80 to 1000 mg KOH/g. Organic acids having an acid value of 60 mg KOH/g or more can more effectively depress the melting point. However, if the acid value of the binder exceeds 1200 mg KOH/g, the melting point depressing effect does not usually increase in accordance with the increase of the acid value.

Preferred binders for use in the invention include neutral or weakly acidic monovalent organic acids, neutral or weakly acidic polycarboxylic acids and neutral or partial salts of weakly acidic polycarboxylic acids, such as (1) monocarboxylic acids, (2) polycarboxylic acids, (3) partial salts of polycarboxylic acids, and the like.

Also usable are phosphoric or phosphorous acid esters, such as (4) esters of phosphoric acid and at least one member selected from the group consisting of $C_1$–$C_{30}$ monohydric aliphatic alcohols and $C_2$–$C_{30}$ polyhydric aliphatic alcohols, (5) esters of phosphorous acid and at least one member selected from the group consisting of $C_1$–$C_{30}$ monohydric aliphatic alcohols and $C_2$–$C_{30}$ polyhydric aliphatic alcohols, (6) esters of phosphoric acid and at least one member selected from the group consisting of $C_6$–$C_{30}$ monohydric aromatic alcohols and $C_6$–$C_{30}$ polyhydric aromatic alcohols, (7) esters of phosphorous acid and at least one member selected from the group consisting of $C_6$–$C_{30}$ monohydric aromatic alcohols and $C_6$–$C_{30}$ polyhydric aromatic alcohols.

(8) Further usable are neutral or weakly alkaline or weakly acidic salts of sulfonic acids, such as taurine.

Other useful binders include salts of strongly acidic organic acids such as salts of sulfuric acid ester, sulfonic acid salts and salts of phosphoric acid ester, in particular (9) salts of $C_4$–$C_{30}$ alkanesulfonic acid or salts of $C_4$–$C_{30}$ alkenesulfonic acid,

(10) ($C_1$–$C_{30}$ alkyl)benzenesulfonic acid salts, and

(11) ($C_1$–$C_{30}$ alkyl)naphthalenesulfonic acid salts,

(12) salts of sulfuric acid ester of a $C_4$–$C_{30}$ saturated aliphatic alcohol or salts of a sulfuric acid ester of a $C_4$–$C_{30}$ unsaturated aliphatic alcohol containing 1 to 3 unsaturated bonds,

(13) salts of sulfuric acid ester of a $C_4$–$C_{30}$ saturated aliphatic alcohol to which 1 to 10 moles of ethylene oxide has been added, or salts of sulfuric acid ester of a $C_4$–$C_{30}$ unsaturated aliphatic alcohol containing 1 to 3 unsaturated bonds, to which 1 to 10 moles of ethylene oxide has been added,

(14) salts of sulfosuccinic acid diester in which the alcohol residue of the ester moieties is a $C_2$–$C_{16}$ alkyl group, cyclohexyl group or a $C_1$–$C_5$ alkyl-substituted cyclohexyl group,

(15) salts of an phosphoric acid ester in which the alcohol residue of the ester moiety or moieties is a $C_4$–$C_{30}$ alkyl group or a $C_4$–$C_{30}$ unsaturated hydrocarbon group containing 1 to 3 unsaturated bonds, or salts of phosphoric acid ester of a $C_5$–$C_{12}$ polyhydric alcohol having 4 to 12 hydroxyl groups,

(16) salts of $C_6$–$C_{30}$ α-sulfo-fatty acid or salts of $C_6$–$C_{30}$ α-sulfo-fatty acid $C_1$–$C_{10}$ alkyl ester. Also usable are

(17) mono-, di- or tri($C_6$–$C_{30}$ fatty acid) aluminum salts.

These binders can be used singly or in combination. If an asymmetric carbon atom is present in the organic acid, it may be the D-isomer, L-isomer or racemic modification.

Among these binders, preferred are neutral or weakly acidic monovalent organic acids, neutral or weakly acidic polycarboxylic acids and neutral or partial salts of weakly acidic polycarboxylic acids, such as (1) monocarboxylic acids, (2) polycarboxylic acids, (3) partial salts of polycarboxylic acids, salts of sulfuric acid ester, sulfonic acid salts and salts of phosphoric acid ester, such as (9) $C_4$–$C_{30}$ alkanesulfonic acid salts or $C_4$–$C_{30}$ alkenesulfonic acid salts,

(10) ($C_1$–$C_{30}$ alkyl)benzenesulfonic acid salts, and

(11) ($C_1$–$C_{30}$ alkyl)naphthalenesulfonic acid salts,

(12) salts of sulfuric acid ester of a $C_4$–$C_{30}$ saturated aliphatic alcohol, or salts of a sulfuric acid ester of a $C_4$–$C_{30}$ unsaturated aliphatic alcohol containing 1 to 3 unsaturated bonds,

(13) salts of sulfuric acid ester of a $C_4$–$C_{30}$ saturated aliphatic alcohol to which 1 to 10 moles of ethylene oxide has been added, or salts of sulfuric acid ester of a $C_4$–$C_{30}$ unsaturated aliphatic alcohol containing 1 to 3 unsaturated bonds, to which 1 to 10 moles of ethylene oxide has been added,

(14) salts of sulfosuccinic acid diester in which the alcohol residue of the ester moieties is a $C_2$–$C_{16}$ alkyl group, cyclohexyl group or a $C_1$–$C_5$ alkyl-substituted cyclohexyl group,

(15) salts of an phosphoric acid ester in which the alcohol residue of the ester moiety or moieties is a $C_4$–$C_{30}$ alkyl group or a $C_4$–$C_{30}$ unsaturated hydrocarbon group containing 1 to 3 unsaturated bonds, or salts of phosphoric acid ester of a $C_5$–$C_{12}$ polyhydric alcohol having 4 to 12 hydroxyl groups,

(16) salts of $C_6$–$C_{30}$ α-sulfo-fatty acid or salts of $C_6$–$C_{30}$ α-sulfo-fatty acid $C_1$–$C_5$ alkyl ester. Also preferably usable are

(17) mono-, di- or tri($C_6$–$C_{30}$ fatty acid) aluminum salts.

The organic acids or derivatives thereof for use in the invention may have one or more bonds other than the carbon-carbon bond (e.g., ether bond, ester bond, thioether bond, amide bond, etc.) or one or more functional groups (e.g., halogen atom, amino group, hydroxyl group, heterocyclic group, carbonyl group, etc.) in the molecule.

In the neutral or weakly acidic organic acids with a valence of two or more (i.e., organic acids having two or more monovalent acid groups in the molecule), part of the acid moieties may form a salt with an alkali metal (e.g., lithium, potassium or sodium), an alkaline earth metal (e.g., calcium), an amine (e.g., triethylamine, trimethylamine or like tri($C_1$–$C_4$ alkyl)amines), ammonium or the like. The strongly acidic organic acids are used usually in the form of salts (i.e., as neutral or weakly acidic salts).

Among these organic acids, mono- and polycarboxylic acids are particularly effective. Most of mono- or polycarboxylic acids are commercially available, safe, hygienic, inexpensive and easy to handle. Thus, they are commercially more advantageous than phosphorous or phosphoric acid compounds or taurine.

Specific examples of the mono- or polycarboxylic acids are aliphatic monocarboxylic acids having 80 or less (preferably 3 to 35) carbon atoms; aliphatic polycarboxylic acids having 80 or less (preferably 4 to 30) carbon atoms, and their alkyl ($C_1$–$C_{22}$) partial esters; aromatic monocarboxylic acids having 80 or less (preferably 7 to 35) carbon atoms; aromatic polycarboxylic acids having 80 or less (preferably 8 to 30) carbon atoms, and their alkyl ($C_1$–$C_{22}$) partial esters; halogen-containing carboxylic acids having 80 or less (preferably 4 to 35) carbon atoms; amino-containing carboxylic acids having 80 or less (preferably 4 to 35) carbon atoms; amide bond-containing carboxylic acids having 80 or less (preferably 4 to 35) carbon atoms; hydroxyl-containing carboxylic acids having 80 or less (preferably 4 to 35) carbon atoms; resin acids; carbonyl-containing carboxylic acids having 80 or less (preferably 4 to 35) carbon atoms; ether bond-containing carboxylic acids having 80 or less (preferably 4 to 35) carbon atoms; ester bond-containing carboxylic acids having 80 or less (preferably 4 to 35) carbon atoms; amide bond- and amino group-containing carboxylic acids having 80 or less (preferably 4 to 35) carbon atoms; amide bond- and hydroxyl group-containing carboxylic acids having 80 or less (preferably 4 to 35) carbon atoms; heterocycle-containing carboxylic acids having 80 or less (preferably 4 to 35) carbon atoms; and thioether bond-containing carboxylic acids having 80 or less (preferably 4 to 35) carbon atoms. Mono- or polycarboxylic acids having more than 80 carbon atoms tend to show insufficient melting point depressing effect, since they usually have a low acid value because of their high molecular weight.

Examples of the aliphatic monocarboxylic acids having 80 or less carbon atoms include propionic acid, butyric acid,- isobutyric acid, valeric acid, n-caproic acid, cyclohexylmonocarboxylic acid, caprylic acid, 2-ethylhexanoic acid, nonanoic acid, capric acid, undecanoic acid, lauric acid, tridecanoic acid, myristic acid, pentadecanoic acid, palmitic acid, heptadecanoic acid, stearic acid, isostearic acid, nonadecanoic acid, octylundecanoic acid, eicosanoic acid, behenic acid, docosahexanoic acid, montanic acid, naphthenic acid, cholanic acid, deoxycholic acid, lithocholic acid, p-tolylacetic acid, diphenylacetic acid, phenoxyacetic acid, benzilic acid, sorbic acid, coconut oil fatty acid, palm oil fatty acid, palm kernel oil fatty acid, beef tallow fatty acid, $C_{22}$–$C_{36}$ carboxylic acids obtained by saponification of rice bran wax, carnauba wax, candelilla wax or bees wax, oleic acid, linoleic acid, linolenic acid, unsaturated fatty acids such as a fatty acid obtained by saponification of fish oil, and their geometrical isomers. Among these examples, recommendable are lauric acid, tridecanoic acid, myristic acid, pentadecanoic acid, palmitic acid, heptadecanoic acid, stearic acid, isostearic acid, eicosanoic acid, behenic acid, docosahexanoic acid, montanic acid, benzilic acid, sorbic acid, oleic acid, linoleic acid and linolenic acid.

Examples of the aliphatic polycarboxylic acids having 80 or less carbon atoms are aliphatic di-, tri- or tetracarboxylic acids, and include glutaric acid, succinic acid, malonic acid, adipic acid, suberic acid, azelaic acid, sebacic acid, dodecanedioic acid, itaconic acid, maleic acid, fumaric acid, citraconic acid, aconitic acid, tricarballylic acid, 1,2,3,4-butanetetracarboxylic acid, citrazinic acid, 1,2,3,4-cyclopentanetetracarboxylic acid, 1,4-cyclohexanedicarboxylic acid, 1,2-cyclohexanedicarboxylic acid, alkyl ($C_1$–$C_8$)-substituted cyclohexanedicarboxylic acid, 4,4'-dicyclohexyldicarboxylic acid, tetrahydrophthalic acid, hexahydrophthalic acid, methyltetrahydrophthalic acid, methylhexahydrophthalic acid, dimer acid, cyclopentanetetracarboxylic acid, cyclohexanetetracarboxylic acid and carboxylic acids obtained by saponification of $C_6$–$C_{80}$ (meth)acrylic acid oligomers or $C_7$–$C_{80}$ methyl (meth)acrylate oligomers. Among these examples, recommendable are succinic acid, glutaric acid, malonic acid, adipic acid, suberic acid, azelaic acid, sebacic acid, dodecanedioic acid, itaconic acid, tricarballylic acid, 1,2,3,4-butanetetracarboxylic acid, citrazinic acid, 1,2,3,4-cyclopentanetetracarboxylic acid, 1,4-cyclohexanedicarboxylic acid, 1,2-cyclohexanedicarboxylic acid, 4,4'-dicyclohexyldicarboxylic acid and cyclohexanetetracarboxylic acid.

Examples of the aromatic monocarboxylic acids having 80 or less carbon atoms are benzoic acid, benzoic acids substituted by 1 to 4 alkyl groups having 1 to 18, preferably 1 to 12 carbon atoms, or by 1 to 2 phenyl groups, such as p-toluic acid, p-ethylbenzoic acid, cuminic acid, p-tert-butylbenzoic acid, p-isobutylbenzoic acid, p-phenylbenzoic acid and 3,5-dimethylbenzoic acid, 1-naphthoic acid, 2-naphthoic acid, tetralinmonocarboxylic acid and alkyl (for example, $C_1$–$C_{12}$)-substituted tetralinmonocarboxylic acid. Among these examples, recommendable are benzoic acid, p-methylbenzoic acid, p-ethylbenzoic acid, p-n-propylbenzoic acid, cuminic acid, p-tert-butylbenzoic acid, p-isobutylbenzoic acid, p-phenylbenzoic acid, 3,5-dimethylbenzoic acid, 1-naphthoic acid, 2-naphthoic acid and tetralinmonocarboxylic acid.

Examples of the aromatic polycarboxylic acids having 80 or less carbon atoms are aromatic di-, tri- and tetracarboxylic acids, and include o-phthalic acid, m-phthalic acid, p-phthalic acid, trimellitic acid, trimesic acid, pyromellitic acid, diphenic acid, benzenehexacarboxylic acid, biphenyldicarboxylic acid, biphenyltetracarboxylic acid, ethylene glycol-4,4'-bistrimellitic acid ditrimellitate, glycyrrhizic acid, naphthalenedicarboxylic acid, diphenylsulfonetetracarboxylic acid, diphenylethertetracarboxylic acid, diphenylmethanetetracarboxylic acid and diphenylpropanetetracarboxylic acid. Among these examples, recommendable are o-phthalic acid, m-phthalic acid, p-phthalic acid, trimellitic acid, trimesic acid, pyromellitic acid, diphenic acid, biphenyldicarboxylic acid, biphenyltetracarboxylic acid, naphthalenedicarboxylic acid, diphenylsulfonetetracarboxylic acid, diphenylethertetracarboxylic acid, diphenylmethanetetracarboxylic acid, diphenylpropanetetracarboxylic acid and ethylene glycol-4,4'-bistrimellitic acid ditrimellitate.

Examples of the halogen-containing carboxylic acids having 80 or less carbon atoms are preferably mono-, di-, tri- or tetracarboxylic acids having about 3 to 24 carbon atoms and containing 1 to 3 halogen atoms such as chlorine or bromine, and include chloropropionic acid, bromopropionic acid, o-chlorobenzoic acid, m-chlorobenzoic acid, p-chlorobenzoic acid, 4-chloro-3-nitrobenzoic acid, diflunisal and trifenamic acid.

Examples of the amino-containing carboxylic acids having 80 or less carbon atoms are preferably mono-, di-, tri- or tetracarboxylic acids having about 2 to 24 carbon atoms and containing 1 to 5 amino groups, and include glycine, alanine, β-alanine, phenylalanine, α-aminoacrylic acid, α-aminobutyric acid, β-aminobutyric acid, γ-aminobutyric acid, alloisoleucine, γ-amino-α-methylenebutyric acid, α-aminoisobutyric acid, β-aminoisobutyric acid, norvaline, δ-amino-n-valeric acid, β-aminocrotonic acid, isoleucine, valine, 2-amino-4-pentenoic acid, norleucine, 6-aminocaproic acid, leucine, 7-aminoheptanoic acid, α-amino-n-caprylic acid, 8-aminocaprylic acid, 9-aminononanoic acid, 11-aminoundecanoic acid, 12-amonododecanoic acid, sarcosine, proline, aminomalonic acid, 2-aminoadipic acid, arginine, aspartic acid, asparagine, cystine, ethionine, cystathionine, lanthionine, glutamine, glutamic acid, theanine, S-(carboxymethyl) cysteine, 2,4-diaminobutyric acid, canavanine, kynurenine, histidine, 1-methylhistidine, 3-methylhistidine, tryptophan, lysine, ornithine, creatine, citrulline, azaserine, allothreonine, threonine, 6-hydroxylysine, homoserine, methionine, ergothioneine, cysteine, cysteic acid, threonine, β-(3,4-dihydroxyphenyl)-alanine and tyrosine, each of which may have D-, L- or DL-configuration, 1-aminocyclohexanecarboxylic acid, 2-aminocyclohexanecarboxylic acid, 3-aminocyclohexanecarboxylic acid, 4-aminocyclohexanecarboxylic acid, p-aminomethylcyclohexanecarboxylic acid, 2-amino-2-norbornanecarboxylic acid, 3,5-diaminocyclohexanecarboxylic acid, 1-amino-1,3-cyclohexanedicarboxylic acid, α-aminophenylacetic acid, α-amino-β-phenylpropionic acid, 2-amino-2-phenylpropionic acid, 3-amino-3-phenylpropionic acid, α-aminocinnamic acid, 2-amino-4-phenylbutyric acid, 4-amino-3-phenylbutyric acid, anthranilic acid, m-aminobenzoic acid, p-aminobenzoic acid, 2-amino-4-methylbenzoic acid, 2-amino-6-methylbenzoic acid, 3-amino-4-methylbenzoic acid, 2-amino-3-methylbenzoic acid, 2-amino-5-methylbenzoic acid, 4-amino-2-methylbenzoic acid, 4-amino-3-methylbenzoic acid, 2-amino-3-methoxybenzoic acid, 3-amino-4-methoxybenzoic acid, 4-amino-2-methoxybenzoic acid, 4-amino-3-methoxybenzoic acid, 2-amino-4,5-dimethoxybenzoic acid, o-aminophenylacetic acid, m-aminophenylacetic acid, p-aminophenylacetic acid, 4-(4-aminophenyl)butyric acid, 4-aminomethylbenzoic acid, 4-aminomethylphenylacetic acid, o-aminocinnamic acid, m-aminocinnamic acid, p-aminocinnamic acid, p-aminohippuric acid, 2-amino-1-naphthoic acid, 3-amino-1-naphthoic acid, 4-amino-1-naphthoic acid, 5-amino-1-naphthoic acid, 6-amino-1-naphthoic acid, 7-amino-1-naphthoic acid, 8-amino-1-naphthoic acid, 1-amino-2-naphthoic acid, 3-amino-2-naphthoic acid, 4-amino-2-naphthoic acid, 5-amino-2-naphthoic acid, 6-amino-2-naphthoic acid, 7-amino-2-naphthoic acid, 8-amino-2-naphthoic acid, 3,5-diaminobenzoic acid, 4,4'-diamino-3,3'-dicarboxydiphenylmethane and ethylenediaminetetraacetic acid. Among these examples, L-glutamine is particularly preferred.

Preferable as the hydroxyl group-containing carboxylic acids having 80 or less carbon atoms are mono-, di-, tri- or tetracarboxylic acids having about 2 to 30 carbon atoms and containing 1 to 5 hydroxyl groups, which may be D-isomer, L-isomer or a racemic modification. Examples thereof are tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid, protocatechuic acid, coumaric acid and like phenolic acids, gallic acid and α,β-dihydroxyhexahydrophthalic acid. Among these examples, recommended are tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid and α,β-dihydroxyhexahydrophthalic acid. Among these preferred examples, particularly recommendable are tartaric acid, lactic acid, malic acid, citric acid and α,β-dihydroxyhexahydrophthalic acid, each of which can significantly depress the melting point of the diacetal by 70 to 100° C. when used in a proportion of 5 wt. % or less (in particular 0.01 to 5 wt. %), more preferably 1 wt. % or less (in particular 0.1 to 2 wt. %), relative to the diacetal.

Examples of the resin acids are dehydroabietic acid, abietic acid, isopimaric acid, levopimaric acid, dihydroabietic acid, neoabietic acid, tetrahydroabietic acid, elliotinoic acid, palustric acid, pimaric acid, sandaracopimaric acid, podocarpic acid, agathenedicarboxylic acid, cinnamic acid and p-oxycinnamic acid. Among these examples, preferred are dehydroabietic acid, abietic acid, dihydroabietic acid, neoabietic acid and tetrahydroabietic acid.

Examples of the carbonyl group-containing carboxylic acids having 80 or less carbon atoms are preferably mono-, di-, tri- or tetracarboxylic acids having about 6 to 30 carbon atoms and containing 1 to 3 carbonyl groups, such as levulinic acid, pyruvic acid and o-benzoylbenzoic acid.

Examples of the ether bond-containing carboxylic acids having 80 or less carbon atoms are preferably mono-, di-, tri- or tetracarboxylic acids having 4 to 18 carbon atoms and containing 1 to 3 ether bonds, such as 4-methoxycyclohexanecarboxylic acid, 4-ethoxycyclohexanecarboxylic acid, p-methoxybenzoic acid, p-ethoxybenzoic acid, p-phenoxybenzoic acid and 2-methoxy-naphthalenecarboxylic acid.

Examples of the ester bond-containing carboxylic acids having 80 or less carbon atoms are preferably mono-, di-, tri- or tetracarboxylic acids having about 6 to 30 carbon atoms and containing 1 to 4 ester bonds, such as acetylcitric acid, stearoylcitric acid, acetylricinolic acid, stearoyllactic acid, citric acid monostearyl ester, citric acid distearyl ester, adipic acid mono-2-ethylhexyl ester, adipic acid monooctyl ester, terephthalic acid monooctyl ester, terephthalic acid monostearyl ester and like polycarboxylic acid partial esters or polycarboxylic acids containing an ester bond in the molecule. Among these examples, recommendable are acetylcitric acid, stearoylcitric acid, acetylricinolic acid, stearoyllactic acid, citric acid monostearyl ester, adipic acid mono-2-ethylhexyl ester and adipic acid monooctyl ester.

Examples of the amide bond- and amino group-containing carboxylic acids having 80 or less carbon atoms are preferably mono-, di-, tri- or tetracarboxylic acids having about 2 to 36 carbon atoms and containing 1 to 4 amide bonds and 1 to 4 amino groups, such as aspartic acid amide, glycyl-alanine, glycyl-α-aminobutyric acid, glycyl-asparagine, glycyl-glutamine, glycyl-glycine, glycyl-glycyl-glycine, glycyl-glycyl-glycyl-glycine, glycyl-leucine, glycyl-norleucine, glycyl-norvaline, glycyl-α-phenylalanine, glycyl-sarcosine, glycyl-tryptophan, alanyl-alanine, alanyl-glutamine, alanyl-glycine, alanyl-glycyl-glycine, β-alanyl-histidine, alanyl-phenylalanine, alanyl-tyrosine and glycine anhydride, each of which may be D-, L- or DL-configuration.

Examples of the amide bond- and hydroxyl group-containing carboxylic acids having 80 or less carbon atoms are preferably mono-, di-, tri- or tetracarboxylic acids having about 2 to 36 carbon atoms and containing 1 to 4 amide bonds and 1 to 4 hydroxyl groups, such as pantothenic acid, citric acid monostearylamide, citric acid distearylamide and like hydroxyl group-containing polycarboxylic acid partial amides.

Preferred as the heterocyclic ring-containing carboxylic acids having 80 or less carbon atoms are preferably mono-, di-, tri- or tetracarboxylic acids having 4 to 18 carbon atoms and containing one 5- or 6-membered heterocyclic ring having 1 to 2 heteroatoms selected from N and S in the hetero ring. Specific examples are nicotinic acid, thioctic acid, proline, oxyproline, suprofen and tiaprofenic acid.

Examples of the thioether bond-containing carboxylic acids having 80 or less carbon atoms are preferably carboxylic acids having about 6 to 30 carbon atoms and containing 1 to 4 thioether groups, such as dithiooctylic acid and thioctic acid.

As the partial salts of the above polycarboxylic acids (namely, polycarboxylic acid salts in which part of the carboxyl groups of the polycarboxylic acid is/are converted to —COOM wherein M is an alkali metal, an alkaline earth metal or a cation), preferable are partial salts of tartaric acid, malic acid, citric acid, succinic acid, glutaric acid, adipic acid, azelaic acid, sebacic acid and the like.

In the present invention, aluminum salts of neutral or weakly acidic monovalent organic acids are recommended, and mono-, di- or tri($C_6$–$C_{30}$, preferably $C_8$–$C_{22}$) fatty acid aluminum salts are preferable. These aluminum salts are represented by the formula $(RCOO)_3Al$, $(RCOO)_2Al(OH)$ or $(RCOO)Al(OH)_2$ wherein RCOO is a residue of $C_6$–$C_{30}$ fatty acid). Among them, there may be mentioned aluminum mono-, di- or tricaproate, aluminum mono-, di- or trienanthate, aluminum mono-, di- or tricaprylate, aluminum mono-, di- or tripelargonate, aluminum mono-, di- or tricaprate, aluminum mono-, di- or tri-undecylate, aluminum mono-, di- or trilaurate, aluminum mono-, di- or tri-tridecylate, aluminum mono-, di- or trimyristate, aluminum mono-, di- or tri-pentadecylate, aluminum mono-, di- or tripalmitate, aluminum mono-, di- or tri-heptadecylate, aluminum mono-, di- or tristearate, aluminum mono-, di- or trioleate, aluminum mono-, di- or tri-nonadecanoate, aluminum mono-, di- or tri-arachate, aluminum mono-, di- or tri-behenate, aluminum mono-, di- or tri-lignocerate, aluminum mono-, di- or tri-cerotate, aluminum mono-, di- or tri-montanate, aluminum mono-, di- or tri-elaidate, aluminum mono-, di- or tri-erucate, aluminum mono-, di- or tri-linoleate, and the like. Among the above examples, mono- or di-carboxylic acid aluminum salts are recommended.

Examples of the sulfonic acid salts for use as the binder in the invention are alkylbenzenesulfonic acid salts or alkylnaphthalenesulfonic acid salts in each of which the alkyl group has 1 to 30, particularly 6 to 14, and preferably 8 to 14, carbon atoms; salts of an alkanesulfonic acid having 6 to 30, preferably 12 to 22 carbon atoms or salts of an alkenesulfonic acid having 6 to 30, preferably 12 to 22 carbon atoms; salts of dialkyl sulfosuccinate in which the alkyl moieties are a $C_3$–$C_{12}$ alkyl group, cyclohexyl group, a $C_1$–$C_3$ alkyl group-substituted cyclohexyl group and the like.

Examples of the salts of sulfuric acid ester are salts of a sulfuric acid ester of a saturated or unsaturated aliphatic alcohol, salts of a sulfuric acid ester with an adduct of ethylene oxide (addition molar number:1–10 moles) and a saturated or unsaturated aliphatic alcohol and the like. Examples of said saturated or unsaturated aliphatic alcohol are those having 4 to 30, in particular 6 to 30, preferably 8 to 20, carbon atoms. It is preferable that the above unsaturated aliphatic alcohol has 1 to 3 unsaturated bonds (particularly double bonds) in the molecule.

Also usable are α-sulfo-fatty acid salts or salts or salts of an α-sulfo-fatty acid $C_1$–$C_{10}$ alkyl (particularly $C_1$–$C_5$ alkyl) ester. The fatty acid constituting them are saturated or unsaturated fatty acid having 6 to 30 carbon atoms. Examples of said α-sulfo-fatty acid salts or their ester salts are in particular salts of α-sulfo-stearic acid, methyl α-sulfo-stearate, butyl α-sulfo-stearate, and the like.

Examples of salts of these sulfonic acids and sulfuric acid esters are lithium, sodium, potassium and other alkali metal salts, ammonium salts, calcium, magnesium and other alkaline earth metal salts.

Examples of the phosphoric acid ester salts are alkali metal salts or alkaline earth metal salts of a phosphoric acid ester in which the alcohol residue(s) of the ester moiety or moieties is(are) a $C_4$–$C_{30}$ alkyl group or a $C_4$–$C_{30}$ unsaturated hydrocarbon group having 1 to 3 unsaturated bonds, or alkali metal salts or alkaline earth metal salts of an ester of phosphoric acid and a $C_5$–$C_{12}$ polyhydric alcohol having 4 to 12 hydroxyl groups, particularly alkali metal salts or alkaline earth metal salts of an ester of phosphoric acid and pentaerythritol or dipentaerythritol. Examples of said alkali metal are sodium, potassium and lithium, and examples of said alkaline earth metal are calcium, magnesium and the like.

Among the above-mentioned binders, the following binders are preferred from the standpoint of the melting point-depressing effect.

(a) Aliphatic monocarboxylic acids having about 8 to 30 carbon atoms, in particular, lauric acid, tridecanoic acid, myristic acid, pentadecanoic acid, palmitic acid, heptadecanoic acid, stearic acid, isostearic acid, eicosanoic acid, behenic acid, docosahexanoic acid, montanic acid, benzilic acid, sorbic acid, oleic acid, linoleic acid, linolenic acid, and the like, (b) Aliphatic dicarboxylic acids having about 3 to 18 carbon atoms, aliphatic tricarboxylic acid having about 6 to 30 carbon atoms or aliphatic tetracarboxylic acid having about 8 to 30 carbon atoms, in particular, succinic acid, glutaric acid, malonic acid, adipic acid, suberic acid, azelaic acid, sebacic acid, dodecanedioic acid, itaconic acid, tricarballylic acid, 1,2,3,4-butanetetracarboxylic acid, citrazinic acid, 1,2,3,4-cyclopentanetetracarboxylic acid, 1,4-cyclohexanedicarboxylic acid, 1,2-cyclohexanedicarboxylic acid, 4,4'-dicyclohexyldicarboxylic acid, cyclohexanetetracarboxylic acid, and the like, (c) Aromatic monocarboxylic acids having about 7 to 15 carbon atoms, in particular, benzoic acid, benzoic acids substituted with 1 to 2 $C_1$–$C_4$ alkyl groups or with one phenyl group (e.g., p-methylbenzoic acid, p-ethylbenzoic acid, n-propylbenzoic acid, cuminic acid, p-tert-butylbenzoic acid, p-isobutylbenzoic acid, p-phenylbenzoic acid and 3,5-dimethylbenzoic acid), 1-naphthoic acid, 2-naphthoic acid, tetralinmonocarboxylic acid and the like, (d) Aromatic di-, tri- or tetracarboxylic acids having about 8 to 20 carbon atoms, in particular, o-phthalic acid, m-phthalic acid, p-phthalic acid, trimellitic acid, trimesic acid, pyromellitic acid, diphenic acid, biphenyldicarboxylic acid, biphenyltetracarboxylic acid, naphthalenedicarboxylic acid, diphenylsulfontetracarboxylic acid, diphenylethertetracarboxylic acid, diphenylmethanetetracarboxylic acid, diphenylpropanetetracarboxylic acid, ethylene glycol-4,4'-bistrimellitic acid ditrimellitate and the like, (e) Halogen-containing carboxylic acids having about 3 to 20 carbon atoms, in particular, aliphatic dicarboxylic acid having about 3 to 18 carbon atoms and containing 1 to 3 halogen atoms, aliphatic tricarboxylic acid having about 6 to 30 carbon atoms and containing 1 to 3 halogen atoms or aliphatic tetracarboxylic acid having about 8 to 30 carbon atoms and containing 1 to 3 halogen atoms, (in which the halogen atom is e.g., chlorine or bromine), in particular chloropropionic acid, bromopropionic acid, o-chlorobenzoic acid, m-chlorobenzoic acid, p-chlorobenzoic acid and 4-chloro-3-nitrobenzoic acid, (f) Mono- or dicarboxylic acids having about 5 to 12 carbon atoms and containing 1 to 3 amino groups, in particular, glutamine, especially L-glutamine, and the like (g) Mono-, di- or tri($C_6$–$C_{30}$ fatty acid) aluminum salts, in particular, di- or mono(carboxylic acid) aluminum salts, among others, aluminum di- or monopelargonate, aluminum di- or monolaurate, aluminum di- or monomyristate, aluminum di- or monostearate, aluminum di- or monooleate, and the like (h) Mono-, di-, tri- or tetracarboxylic acids having about 4 to 24 carbon atoms and containing 1 to 5 hydroxyl groups, in particular, tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid, α,β-dihydroxyhexahydrophthalic acid and the like, (i) Resin acids, in particular, dehydroabietic acid, abietic acid, dihydroabietic acid, neoabietic acid, tetrahydroabietic acid and the like, (j) Mono- or dicarboxylic acids having about 4 to 18 carbon atoms and containing 1 to 3 carbonyl groups, in particular, mono- or dicarboxylic acids having about 5 to 14 carbon atoms and containing 1 to 2 carbonyl groups, such as levulinic acid, pyruvic acid, o-benzoylbenzoic acid and the like, (k) Mono- or dicaroxylic acids having about 8 to 15 carbon atoms and containing 1 to 2 ether bonds (in particular, mono- or dicarboxylic acids containing 1 to 2 $C_1$–$C_4$ alkoxy groups and having 8 to 15 carbon atoms in total), in particular 4-methoxycyclohexanecarboxylic acid, 4-ethoxycyclohexanecarboxylic acid, p-methoxybenzoic acid, p-ethoxybenzoic acid, p-phenoxybenzoic acid and the like, (l) Mono- or dicarboxylic acids having about 5 to 26 carbon atoms and containing 1 to 2 ester bonds, in particular acetylcitric acid, stearylcitric acid, acetylricinolic acid, stearoyllactic acid, citric acid monostearyl ester, adipic acid mono-2-ethylhexyl ester and adipic acid monooctyl ester, and the like, (m) (m-1) Alkali metal salts, ammonium salts, and alkaline earth metal salts, such as calcium salts and magnesium salts, of $C_6$–$C_{30}$ alkanesulfonic acid, of $C_6$–$C_{30}$ alkenesulfonic acid, of ($C_1$–$C_{22}$ alkyl)benzenesulfonic acid and of ($C_1$–$C_{14}$ alkyl)naphthalenesulfonic acid, and (m-2) salts of a sulfuric acid ester of a $C_6$–$C_{30}$ saturated or unsaturated aliphatic alcohol; salts of sulfuric acid ester of an adduct of 1 to 10 moles of ethylene oxide and a $C_6$–$C_{30}$ saturated or unsaturated aliphatic alcohol; salts of sulfosuccinic acid diester (in particular salts of sulfo-succinic acid diester in which the alcohol residues of the ester moieties are a $C_2$–$C_{16}$ alkyl group, cyclohexyl group or a $C_1$–$C_5$ alkyl group-substituted cyclohexyl group); α-sulfofatty acid salts or salts of α-sulfo-fatty acid ester (in particular, $C_6$–$C_{30}$ α-sulfo-fatty acid salts or salts of $C_6$–$C_{30}$ α-sulfofatty acid $C_1$–$C_{10}$ alkyl ester), in which the cation constituting these salts is, for example, an alkali metal such as potassium and sodium, ammonium and an alkaline earth metal such as calcium and magnesium, among others (mm) a potassium or sodium salt of a $C_{18}$ alkane- or alkene-sulfonic acid, sodium dodecylbenzenesulfonate, sodium dodecylsulfate, sodium dodecyl ether sulfate (namely, sodium salt of sulfuric acid ester of dodecyl alcohol to which 1 mole of ethylene oxide has been added, sodium dioctyl sulfo-succinate, sodium methyl α-sulfo-stearate, and the like.

The above binders (a) to (m) can be used singly or at least two of them may be used in combination.

Among the above binders, preferred is/are (h) at least one member selected from mono-, di-, tri- or tetracarboxylic acids having 4 to 24, preferably 4 to 12 carbon atoms and containing 1 to 5, preferably 1 to 4 hydroxyl groups, in particular, tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid or α,β-dihydroxyhexahydrophthalic acid, or the binders set forth in item (m).

Also preferred is at least one member selected from the group consisting of (h-a) tartaric acid, lactic acid, malic acid, citric acid, succinic acid and α,β-dihydroxyhexahydrophthalic acid, at least one member selected from the group consisting of the binders set forth in item (m), particularly in item (mm), or a mixture of (h-a) and (mm).

The binders set forth in items (a) to (m), particularly the binders set forth in item (h) or the binders set forth in item (m), exhibit the melting point depressing effect when used in a proportion of usually about 0.01 to 8 wt. parts, preferably about 0.1 to 5 wt. parts, more preferably about 0.1 to 1.0 wt. part, per 100 wt. parts of the diacetal represented by the formula (1).

As preferred binders to be used in t he present invention, there may be mentioned the following ones.

1) at least one binder selected from the group consisting of the binders set forth in item (h) and the binders set forth in item (a),
2) at least one binder selected from the group consisting of the binders set forth in item (h) and the binders set forth in item (b),
3) at least one binder selected from the group consisting of the binders set fo rth in item (h) and the binders set forth in item (m),
4) at least one binder selected from the group consisting of the binders set forth in item (m) and the binders set forth in item (a), 5) at least one binder selected from the group consisting of the binders set forth in item (m),
6) at least one binder selected from the group consisting of the binders set forth in item (m) and the binders set forth in item (g),
7) at least one binder selected from the group consisting of the binders set forth in item (g) and the binders set forth in item (a).

Either when the binder is used singly or when at least 2 of the binders are used in combination, the amount of the binder used in the present invention is not particularly limited, insofar as the contemplated effects of the present invention can be achieved, and can be suitably selected according to the kinds of the diacetal and organic acid and the derivative thereof. The amount of the binder is usually 0.01 to 100 wt. parts, preferably 0.1 to 70 wt. parts, more preferably 0.2 to 25 wt. parts, per 100 wt. parts of the diacetal of the formula (1). If the amount of the binder is less than 0.01 wt. part, both melting point depressing effect and binder effect are difficult to obtain, while an amount exceeding 100 wt. parts brings no specific advantages in binder effect and melting point depressing effect and tends to decrease the polyolefin-nucleating effect.

The binders set forth in item (h) or the binders set forth in item (m) exhibit the melting point depressing effect even when used in a particularly small amount.

Granular or Powdery Diacetal Composition

The granular or powdery diacetal composition of the invention comprises the diacetal of the formula (1) and the above binder, and the binder uniformly permeates among the fibrous crystals of the diacetal. Consequently, the binder is uniformly dispersed not only on the surface of the diacetal particles but also in the interior of the diacetal particles. The more uniformly the binder is dispersed, the larger the melting point depressing effect becomes.

It is well known that when a pure material (X) is mixed with a second material (Y), the melting point of the pure material (X) is depressed (freezing point depression). The decrement in the melting point depends on the molar concentration of (Y). When 10 wt. parts of (Y) is added to 90 wt. parts of the diacetal represented by the formula (1), the melting point of the diacetal is usually depressed only by about 2 to 3° C., or 5° C. at most.

In contrast, the diacetal composition prepared by uniformly dispersing the binder in the diacetal of the formula (1) according to invention has a melting point lower than that of the diacetal itself contained in said composition by usually 7° C. or more, preferably 20° C. or more, more preferably 40° C., especially 50° C. or more, in particular 70° C. or more, most preferably 90° C. or more. It is therefore assumed that, according to the invention, the melting point of the diacetal is depressed by a mechanism resulting from a unique interaction, the mechanism being different from that of normal freezing point depression. In particular, the mechanism of the melting point depression by 50° C. or more remains to be elucidated. In any event, the binder according to the invention exhibits the effect of depressing the melting point of the diacetal by 7° C. or more, preferably 20° C. or more, more preferably and remarkably 90° C. or more, only when the fibrous crystals of the diacetal represented by the formula (1) is swelled and the binder is uniformly distributed among the fibrous crystals. The maximum melting point depression varies according to the kind and amount of the binder to be used, the method of preparing the composition and the like, and thus is not limited, but is usually about 100° C. As a result, the melting point of the diacetal composition of the invention usually varies from about 185 to about 230° C.

According to the present invention, the dissolution rate of the diacetal in molten resins or various fluids can be significantly increased by the melting point depression of the diacetal by at least 7° C., preferably 20° C. or more, more preferably 40° C. or more, and still more preferably 90° C. or more. The reason is that, at a temperature higher than the melting point of the polyolefin, mixing of a solid diacetal and a molten polyolefin liquid is converted into mixing of a liquid and a liquid. In other words, a solid diacetal having a high melting point has conventionally been dissolved in a liquid such as a molten polyolefin resin during molding process. According to the invention, however, the melting point of the diacetal is remarkably depressed, and therefore the temperature of the molten polyolefin is generally higher than the melting point of the diacetal composition of the invention, with the result that the diacetal melts and dissolves in the molten polyolefin within a very short period after adding the diacetal composition of the invention to the molten polyolefin and, in some cases, substantially at the same time as or immediately after the addition. The molten diacetal is dissolved in the molten polyolefin by liquid-liquid mixing.

Since the dissolution occurs at a considerably low temperature, the diacetal does not decompose, sublimate, or cause coloration, for example, in the polyolefin resin molding process. Further, the low temperature molding is energy-saving.

The diacetal composition of the invention may be in powder form or may be in the form of granulated product of any shape, such as noodles, granules or tablets. When the composition is in powder form, the average value of the diameters of the particles of the powdery composition is 3 to 2000 $\mu$m, preferably 3 to 500 $\mu$m, in particular 5 to 500 $\mu$m, more preferably 7 to 250 $\mu$m. When the average value is less than 3 $\mu$m, the flow property and transferability of the powdery composition and suppression of dust are sometimes insufficient, and furthermore a special pulverizer is required.

The average value of the diameters of the particles of the powdery composition is a median diameter determined with a particle size distribution measuring apparatus with a laser diffraction/scattering (trade name "LA-910", product of Horiba, Ltd.) using distilled water as a dispersion medium. In this specification, said average value of the diameters of the particles is simply referred to as "average particle diameter".

The particle size distribution of the powdery composition may be wide, and need not be monodisperse. The powdery composition is sufficiently usable, if having a particle size distribution obtainable with an ordinary pulverizer for industrial use.

When the composition of the invention is a granulated product, the particles are, for example, cylindrical or noodle-shaped particles with a sectional diameter of 0.2 to 5 mm, preferably 0.5 to 2 mm and a length of 0.2 to 15 mm, or granules or flakes with a diameter of 0.2 to 5 mm, preferably 0.5 to 2 mm.

Preferred bulk density of the diacetal composition of the invention is, for example, 0.2 to 1.1 g/cm$^3$, more preferably 0.2 to 0.75 g/cm$^3$. If the bulk density is less than 0.2 g/cm$^3$, flow property and transferability, suppression of dust and adhesion of the powdery composition tend to be insufficient. On the other hand, if the bulk density exceeds 1.1 g/cm$^3$, the composition has remarkably improved powder properties but is likely to have slightly lower speed of dissolution in molten resins or other fluids. The bulk density of the diacetal composition can be desirably controlled by selecting the drying temperature, drying conditions or granulation process for preparation of the diacetal composition of the present invention. Specifically, the bulk density tend to become high when the drying is carried out at a low speed and at a high temperature, while the bulk density tends to become low when the drying is carried at a high speed and at a low temperature. When the compression ratio for granulation is large, the bulk density becomes high.

If desired, the granular diacetal composition of the invention may contain, in addition to the above binder, various additives such as an antistatic agent, a neutralizing agent or a stabilizer, a lubricant and a polymer.

The above antistatic agent may be used in the invention for the purpose of improving the degree of swelling and the uniformity of the diacetal composition during the production thereof so as to enhance the binder effect and melting point depressing effect and increase the stability of the quality of the diacetal composition; or for the purpose of eliminating electrostatic property of the diacetal composition; or for the purpose of increasing the bulk density of the diacetal composition. These effects are important for further improving the stability of the quality, transferability and flow property.

Specific examples of such antistatic agents include glycerin fatty acid ($C_8$–$C_{22}$) mono-, di- and triesters, sorbitan aliphatic ($C_4$–$C_{22}$) mono-, di-, tri- and tetraesters, polypropylene glycol fatty acid ($C_8$–$C_{22}$) esters, pentaerythritol fatty acid ($C_8$–$C_{22}$) esters, trimethylolpropane fatty acid ($C_8$–$C_{22}$) esters, polyglycerine fatty acid ($C_8$–$C_{22}$) esters, polyoxyethylene (4–50 moles) alkyl($C_7$–$C_{22}$)phenyl ethers, polyoxyethylene (4–50 moles) alkyl($C_{12}$–$C_{22}$) ethers, N,N-bis(2-hydroxyethyl)alkyl($C_8$–$C_{22}$)amines, polyoxyethylene (4–50 moles)monoalkyl($C_7$–$C_{22}$)amines, polyethyleneglycol (4–50 moles) fatty acid($C_8$–$C_{22}$) esters, sulfates (sodium, potassium and ammonium salts), sorbitan mono-, di- and tri-fatty acid ($C_4$–$C_{22}$) esters.

Among these antistatic agents, particularly preferred are glycerine fatty acid ($C_8$–$C_{22}$) mono-, di- and triesters, N,N-bis(2-hydroxyethyl)alkyl($C_8$–$C_{22}$) amines, polyoxyethylene (4–50 moles) alkyl ($C_{12}$–$C_{22}$) ethers, polyoxyethylene (4–50 moles) alkyl ($C_7$–$C_{22}$) phenylethers and pentaerythritol fatty acid ($C_8$–$C_{22}$) esters.

The antistatic agent is used in an amount of preferably 0.01 to 50 wt. parts, more preferably 0.1 to 20 wt. parts, per 100 wt. parts of the diacetal represented by the formula (1). The antistatic agent not only eliminates the electrostatic property but also effectively increases the bulk density by enhancing the binder effect due to the increase of the degree of swelling.

Examples of the neutralizing agent or stabilizers include metallic soaps, phenol compounds, phosphorus compounds, sulfur compounds, such as calcium stearate, lithium stearate, potassium stearate, sodium stearate, tetrakis[methylene-3-(3',5'-di-t-butyl-4'-hydroxyphenyl)propionato]methane, tris(2,4-di-t-butylphenyl)phosphite, distearyl 3,3'-thiodipropionate. The neutralizing agent or stabilizer is used in an amount of about 5 to 100 wt. parts, preferably about 15 to 70 wt. parts, per 100 wt. parts of the diacetal represented by the formula (1).

Examples of the above lubricant include hardened oils, such as hardened castor oil, hardened rapeseed oil, hardened palm oil, hardened beef tallow, hardened cottonseed oil, hardened soybean oil, or the like. The lubricant is used in an amount of about 1 to 20 wt. parts, preferably about 3 to 10 wt. parts, per 100 wt. parts of the diacetal represented by the formula (1).

Examples of the above polymers include polyethylenes and polypropylenes having a molecular weight of 10000 or less, hydrogenated petroleum resins, ethylene-propylene rubbers and the like. The polymer is used in an amount of about 5 to 10000 wt. parts, preferably about 100 to 5000 wt. parts, per 100 wt. parts of the diacetal represented by the formula (1).

In the diacetal composition of the present invention, the use of the above binder in combination with at least one member selected from the group consisting of said antistatic agents, neutralizing agents or stabilizers and lubricant will increase the binder effect in addition to the melting point depressant effect. In this case, the binders may be any of those mentioned above, and especially the binders set forth in items (a) to (m) may be used singly or at least two of them may be used in admixture.

Especially, it is preferable to use (I) at least one binder selected from the group consisting of the binders set forth in item (h-a), the binders set forth in item (m), the binders set forth in item (a) and the binders set forth in item (g) in combination with (II) said hardened oil which is a lubricant.

In this case, the proportions of (I) and (II) are not particularly limited, but it is generally recommended to use (II) in an amount of about 10 to 10000 wt. parts, per 100 wt. parts of (I).

When (I) is used in combination with (II), it is recommended that, per 100 wt. parts of the diacetal represented by the formula (1), (I) is used in an amount of about 0.1 to 30 wt. parts, preferably about 0.4 yo 20 wt. parts, and (II) is used in an amount of about 0.5 to 25 wt. parts, preferably about 2 to 10 wt. parts, whereby excellent melting point depressing effect and binder effect are achieved.

Of the above combinations, it is preferable to use at least one member selected from the group consisting of the binders set forth in item (h-a), the binders set forth in item (m) and the binders set forth in item (a) in combination with said hardened oil.

It is further preferable to use at least one member selected from the group consisting of the binders set forth in item (m) and the binders set forth in item (a) in combination with said hardened oil.

It is also preferable to use at least one member selected from the group consisting of the binders set forth in item (a), the binders set forth in item (g) and the binders set forth in item (m) in combination with said hardened oil.

Process for Preparing Diacetal Composition

For preparing the diacetal composition of the invention, the binder needs to be uniformly dispersed in the interior of the crystal powder particles to every minute part thereof, i.e., among the interspaces of the fibrous crystals of the diacetal, so as to achieve the contemplated effects of the invention.

Therefore, a preferred preparation process of the invention is characterized in that it comprises the steps of sufficiently swelling the starting diacetal crystals with a solvent; mixing the swelled diacetal with the binder, and if desired, an additive or additives (which may be in the form of a melt or a solution) such as an antistatic agent; granulating the resulting mixture while drying it (for removing the solvent and water) to give a diacetal composition, and if desired, pulverizing or classifying the granulated diacetal composition, or further granulating the pulverized diacetal composition.

In particular, the granular or powdery diacetal composition of the invention can be prepared, as a product having a desired particle size distribution, by the process comprising the steps of:

(i) preparing a slurry containing a diacetal of the formula (1) swelled with a solvent, (ii) uniformly mixing the above slurry with a binder, (iii) (a) removing the solvent from the resulting uniform mixture to obtain a dry product, or (b) granulating the resulting uniform mixture while removing the solvent therefrom, or (c) pulverizing or classifying the dry product obtained in the step (a) or the granulated product obtained in the step (b), or (d) granulating or sifting the pulverized product obtained by the step (c).

As preferred processes for preparing the diacetal composition of the present invention, there may be mentioned the following three processes.

Process (1)

A process comprising the steps of sufficiently agitating and mixing a slurry comprising a diacetal represented by the formula (1) and an organic solvent capable of swelling the diacetal represented by the formula (1), with heating at 20 to 200° C., preferably 100° C. or lower, i.e., a temperature around the reflux temperature of said organic solvent (for example, about 60 to 100° C.) to swell the diacetal; adding to, and dissolving in this system a binder and if desired an additive or additives such as an antistatic agent; totally and uniformly dispersing the binder and if desired the additive or additives in the system; granulating the resulting mixture, while adding water to the mixture when so required, and while drying said mixture with stirring by distilling off the organic solvent and the water at a temperature in the range of, for example, 20 to 180° C.; and sifting the granulated product; and if desired, pulverizing the granulated product and sifting the obtained powder, or further granulating the obtained powder.

In the above process, a powdery diacetal can be used as the starting diacetal. The particles of the powdery diacetal are composed of dense aggregates of fibrous diacetal microcrystals. When such aggregates of diacetal microcrystals are fully swelled with the organic solvent at the above specified temperature, they substantially separate into the individual fibrous crystals while the solvent penetrates into the interstices of the fibrous crystals, whereby the crystal is swelled.

In this way, the binder and an optionally used additive or additives such as an antistatic agent are added to the slurry wherein the diacetal crystals are swelled with the organic solvent and separated into individual fibrous crystals in the organic solvent, and the swelled diacetal crystals and dissolved binder (and a dissolved or dispersed additive or additives such as an antistatic agent) are mixed until the mixture becomes uniform, and then the solvent is removed, followed by granulation. The diacetal composition of the invention is thus obtained in which the binder and the optional additive or additives such as the antistatic agent are dispersed in the diacetal particles in a uniform distribution.

Sufficient swelling of the fibrous crystals of diacetal is particularly important to achieve the maximum melting point depression. When a diacetal is dispersed in a non-polar solvent such as a cyclohexane solvent and thoroughly stirred at room temperature, the viscosity of the system does not rapidly increase with time. In other words, the non-polar solvent such as a cyclohexane solvent does not permeate among the diacetal fibrous crystals in a large amount, and the swelling of the diacetal does not occur. Under the circumstances, addition of the binder, followed by drying, does not result in such a large melting point depression as described above.

On the other hand, when a diacetal is dispersed in a mixture of a non-polar solvent such as a cyclohexane solvent with a polar solvent, and the dispersion is stirred with heating, then the viscosity of the system rapidly increases with time. In other words, said solvent mixture permeates into the interspaces among the diacetal fibrous crystals in a large amount, with the result that the swelling of the diacetal develops. When a binder is added to the sufficiently swelled diacetal and the mixture is dried, the desired melting point depression can be achieved. A larger melting point depression results with an increasing swelling degree of the diacetal. Of course, the swelling of the diacetal can be done by a polar solvent alone.

Thus, in the present invention, as the solvent for swelling, a polar organic solvent alone is used, or an aromatic hydrocarbon solvent alone is used, or a mixture of (a) at least one member selected from the group consisting of polar organic solvents and aromatic hydrocarbons and (b) at least one member selected from the group consisting of aliphatic hydrocarbons and alicyclic hydrocarbons is used.

Examples of the above polar solvent are $C_1$–$C_{18}$, preferably $C_1$–$C_5$, in particular $C_1$–$C_3$ aliphatic alcohols, such as methanol, ethanol, isopropanol and butanol; $C_6$–$C_{18}$, $C_6$–$C_{12}$ preferably alicyclic alcohols such as cyclobutanemethanol, cyclohexanol and methylcyclohexanol; furfuryl alcohol; cyclic ethers such as dioxane; ethers such as anisole; ketones such as acetone, methyl ethyl ketone; aliphatic amines having about 3 to 6 carbon atoms; acetonitrile; glycol ethers such as ethylene glycol monomethyl ether; dimethylformamide (DMF), dimethylacetamide (DMAc), diemthylsulfoxide (DMSO), N-methylpyrrolidone (NMP) and the like.

Examples of the aromatic hydrocarbons are $C_6$–$C_{18}$, preferably $C_6$–$C_{12}$, aromatic hydrocarbons such as toluene, xylene, mesitylene, ethylbenzene and isopropylbenzene.

Examples of the aliphatic hydrocarbons and alicyclic hydrocarbons include $C_6$–$C_{18}$, preferably $C_6$–$C_{12}$ aliphatic hydrocarbons such as n-hexane, heptane, nonane and decane, $C_6$–$C_{18}$, preferably $C_6$–$C_{12}$ alicyclic hydrocarbons such as cyclohexane, methylcyclohexane and ethylcyclohexane.

It is recommendable that the slurry concentration is 1 to 60 wt. %, preferably 5 to 60 wt. %, more preferably 10 to 40 wt. %, calculated as the diacetal. A concentration less than 1 wt. % results in inefficient production and is not economical, whereas if the concentration exceeds 65 wt. %, the diacetal is not sufficiently swelled, making it difficult to stir.

Sufficient swelling of the diacetal in the slurry can be easily confirmed. That is, the diacetal is confirmed as being sufficiently swelled when the slurry viscosity rapidly increases at a low shear rate, or when the slurry does not separate into two phases even after being allowed to stand. Alternatively, microscopic observation can be employed to confirm that the solvent is absorbed or impregnated among the loosened fibrous microcrystals.

After the diacetal swells, the binder and the optional additive or additives such as an antistatic agent are added, whereby they dissolve or disperse in the organic solvent in the slurry. The obtained mixture is stirred until the mixture becomes uniform.

The binder and the optional additive or additives may be added as such, or may be added in the form of a solution in an organic solvent capable of dissolving the binder and the optional additive or additives, in the form of a dispersion in an organic solvent, or in the form of a melt. Examples of useful organic solvents includes the organic solvents used for swelling and water.

The amount of the binder is usually 0.01 to 100 wt. parts, preferably 0.1 to 70 wt. parts, more preferably 0.2 to 25 wt. parts, per 100 wt. parts of the diacetal represented by the formula (1). The additives such as an antistatic agent, a neutralizing agent or a stabilizer, a lubricant and a polymer, when employed, are used in the amount described above. For example, the antistatic agent is used in an amount of preferably 0.01 to 50 wt. parts, more preferably 0.1 to 20 wt. parts, per 100 wt. parts of the diacetal represented by the formula (1).

The temperature of the slurry is not particularly limited, but a recommended temperature is usually room temperature to about 150° C., preferably room temperature to about 100° C.

Subsequently, the organic solvent is removed from the slurry, for example, by one of the following methods.

(a) Water is added, when so required, to the slurry containing the swelled diacetal, binder, optional additive or additives such as an antistatic agent, a neutralizing agent or stabilizer, a lubricant and a polymer (hereinafter referred to simply as "additives such as an antistatic agent") in the organic solvent. The organic solvent and water (when added) are completely distilled off, for example, at 30 to 150° C., preferably 40 to 120° C. for drying. The resulting dry product is the diacetal composition of the invention.

(b) Water is added to the slurry containing the swelled diacetal, binder, optional additives such as an antistatic agent In the organic solvent. Then, most of the organic solvent is distilled off, with heating where necessary (for example at 40 to 150° C., preferably 40 to 120° C.), to obtain a residue wet with water. The wet residue is granulated by drying the wet residue with stirring and if desired with heating (for example at 40 to 150° C., preferably 40 to 120° C.). The thus-obtained granulated product is the diacetal composition of the invention.

Water is added in the process (a) when so required, and water is added in the process (b), in order to i) facilitate the control of the apparent density of the diacetal composition for imparting a high density thereto, and ii) recover the organic solvent efficiently so as to give nonflammable wet cake, eliminating the possibility of ignition at the time of drying. In view of the above, when water is used, the amount of water is not limited, but is usually about 20 to 1000 wt. parts, preferably about 40 to 600 wt. parts, per 100 wt. parts of the diacetal represented by the formula (1).

In the present invention, the diacetal composition of the invention in the form of the dry product obtained in the process (a) or the granulated product obtained in the process (b) can be, where necessary, classified or pulverized, and the pulverized product can be classified. Further, where necessary, the dry product obtained in the process (a) or the pulverized product can be further granulated with or without addition of water or a volatile organic solvent such as methanol or ethanol.

Process (2)

When a polyhydric alcohol such as sorbitol or xylitol and an aromatic aldehyde such as benzaldehyde or a substituted benzaldehyde are subjected to a condensation reaction, by a known process for preparing diacetals (such as one disclosed in Japanese Examined Patent Publication No. 43748/1973 and Japanese Unexamined Patent Publication No. 231488/1990), in an organic solvent such as cyclohexane, saturated hydrocarbons, benzene, cyclohexane or benzene having 1 to 3 alkyl groups each having 1 to 4 carbon atoms, in the presence of a polar organic solvent such as a lower (e.g., $C_1$–$C_4$) alcohol (such as methanol), dimethylformamide (DMF), dimethylacetamide (DMAc), dimethylsulfoxide (DMSO), N-methylpyrrolidone (NMP) or the like, and if desired in the presence of an acid catalyst, the resulting reaction mixture (which is preferably obtained after neutralizing the acid catalyst and washing the obtained reaction mixture with water) is in the form of a slurry comprising a diacetal swelled with the above solvent.

Also, in the course of purification of a diacetal in an organic solvent such as a lower aliphatic ketone or a lower aliphatic alcohol according to known processes (for example, Japanese Unexamined Patent Publications Nos. 5165/1978 and 185287/1982), a slurry comprising a diacetal swelled with the above organic solvent is obtained.

According to the invention, the binder and if desired the additives such as an antistatic agent (which may be in the form of a melt or a solution or uniform dispersion) is(are) added to, and fully and uniformly dispersed in, said slurry containing the swelled diacetal represented by the formula (1).

Then, (i) from the slurry containing the binder and if desired the additives such as an antistatic agent, as such or as mixed with water, the organic solvent or water (when contained) are distilled off at 20 to 180° C., and the residue is granulated while drying it, with heating where necessary (for example at about 40 to 150° C., preferably about 40 to 100° C.). The granulated product is classified if so desired. The classified product may be pulverized. The pulverized product may be classified or further granulated.

Alternatively, (ii) water is added to the slurry containing the binder and if desired additives such as an antistatic agent. The organic solvent is distilled off from the system by azeotropy of water and the organic solvent, so that the system is converted into an aqueous dispersion system. The aqueous dispersion system, after or without filtration, is granulated while being dried at a temperature in the range of, for example, 20 to 180° C. The resulting granulated product is classified or pulverized when so required. The pulverized product may be classified or further granulated.

In the processes (i) and (ii), when water is used, the amount of water is about 20 to 1000 wt. parts per 100 wt. parts of the diacetal represented by the formula (1).

The binder and if desired the additives such as an antistatic agent may be added at any stage of the process without any particular limitations, insofar as the contemplated results can be achieved. Preferably, as the above-mentioned diacetal swelled with an organic solvent, there may be recommended a diacetal obtained by completing the acetalizatin reaction, neutralizing the acid catalyst and washing the reaction mixture with water. When the binder and optional additives such as an antistatic agent are added in the course of the purification process, they are added preferably after the system becomes a swelled slurry.

The amounts of the binder and the optional additives such as an antistatic agent are the same as in the process (1). After adding the binder and if desired additives such as an antistatic agent, the subsequent procedure is carried out in a similar manner to that of the process (1) (procedure comprising, for example, removing the solvent (drying) to obtain a dry product, or granulating the slurry while removing the solvent (drying), or classifying or pulverizing the resulting dry product or granulated product, or granulating or classifying the obtained pulverized product, etc.), to obtain the diacetal composition of the invention wherein the binder and if desired the additives such as an antistatic agent are uniformly dispersed in the particles of the diacetal.

Process (3)

A process comprising the steps of: synthesizing the diacetal of the formula (1) by a reaction using an aqueous system; neutralizing and washing with water the reaction mixture to give an aqueous slurry of the diacetal swelled with water; adding the binder and if desired additives such as an antistatic agent followed by stirring at room temperature or with heating to give a uniform slurry; filtering the uniform slurry to obtain a wet cake when so required; and drying the uniform slurry or the wet cake to obtain a dry product, or drying the uniform slurry or wet cake with stirring for granulation. The dry product or the granulated product is the diacetal composition of the invention. Where necessary, the composition of the invention in the form of the dry product or granulated product can be classified or pulverized, or the pulverized product can be classified or granulated when so required.

The reaction using an aqueous system is described, for example, in U.S. Pat. No. 5,023,354. Briefly, it has a feature of reacting an optionally substituted benzaldehyde with a polyhydric alcohol such as sorbitol using water as a solvent and in the presence of an acid catalyst in an amount of as large as 10 wt. % or more relative to the reaction substrates.

The above aqueous slurry is obtained by neutralizing the reaction mixture obtained by said reaction using an aqueous system and washing the neutralized reaction mixture with water. The aqueous slurry is swelled with water and comprises fibrous crystals unique to diacetals with a large amount of water permeated among the crystals.

The binder and if desired the additives such as an antistatic agent to be uniformly dispersed in the aqueous slurry of diacetal obtained by said reaction using an aqueous system are preferably hydrophilic.

Examples of such hydrophilic binders include hydroxyl group-containing polycarboxylic acids with a valency of two or more, preferably di-, tri- or tetracarboxylic acids having about 3 to 10 carbon atoms and containing 1 to 3 hydroxyl groups. Among them, particularly preferred are L-tartaric acid, D-tartaric acid, DL-tartaric acid, D-, L- or DL-lactic acid, D-, L- or DL-malic acid, D-, L- or DL-citric acid and α, β-dihydroxyhexahydrophthalic acid. Also preferable are alkyl ($C_6$–$C_{14}$) sulfuric acid salts, sodium alkyl(average chain length of 12)benzenesulfonate which may contain sodium sulfate, or the like.

Examples of hydrophilic additives include antistatic agents such as stearic acid monoglyceride, stearic acid diglyceride, oleic acid monoglyceride, oleic acid diglyceride, myristic acid monoglyceride, myristic acid diglyceride, lauric acid monoglyceride, lauric acid diglyceride, polyethylene glycol monostearate, or the like.

The hydrophilic binder is used in an amount of preferably about 0.1 to 10 wt. parts, more preferably about 0.2 to 5 wt. parts, per 100 wt. parts of the diacetal represented by the formula (1). The hydrophilic additive such as an antistatic agent is used in an amount of preferably 0.01 to 8 wt. parts, more preferably 0.1 to 5 wt. parts, per 100 wt. parts of the diacetal represented by the formula (1).

However, even when the binder and the additives which is used if so desired are lipophilic, they can be used.

In the above processes (1) to (3), the method of granulating the slurry or wet cake while drying the slurry or wet cake with stirring is not limited, insofar as the organic solvent or water can be removed. Conventional methods employed for industrial purposes can be utilized. For example, the slurry or wet cake is granulated while drying it with stirring and with heating at 20 to 180° C. with steam or a heat transfer medium for about 1 to 20 hours under normal or reduced pressure.

The slurry or wet cake may be dried without stirring, but it is preferable to dry and granulate the slurry with stirring from an industrial viewpoint.

The method of granulation of the powder after drying is not limited, insofar as the contemplated results of the invention can be achieved. Usually, however, the powder can be granulated with a granulating machine generally used for industrial purposes. In this case, water or an organic solvent may be used to wet the diacetal powder. The granulating machine may be, for example, any of various extrusion moulder and compression moulder such as tableting machines.

The method for pulverization is not limited insofar as the contemplated effects of the invention can be achieved. Various pulverizing equipments generally used for industrial purposes can be used, which include atomizers, pulverizers, nibblers, hammer mills, micron mills, cross flow mills and pin mills.

Polyolefin Resin Nucleating Agent

The powdery or granulated diacetal composition of the invention obtained by the above processes has a remarkably lower melting point than that of the diacetal because of the melting point depressing effect of the binder uniformly dispersed throughout the diacetal particles.

As a result, the composition of the invention has an increased dissolution rate in molten resins or various fluids, and has a significantly improved solubility and dispersibility. At the same time, the composition has an increased bulk density due to the binder effect, and thus can be compactly packaged. When so required, the powdery diacetal composition can be formed into granules with a desired shape and size, using any of various extrusion granulator or compression moulder. The powdery or granulated diacetal composition is increased in flow property and transferability, suppressed in dust generation and improved in solid properties such as suppression of adhesion to glass and metals. Further, the composition of the invention, when containing additives such as an antistatic agent, has improved handling properties as a solid.

In view of the above, compared with the processing in which an ordinary diacetal is added to a polyolefin resin, the diacetal composition of the invention, when used as a nucleating agent for polyolefin resins, gives good feeding transferability, and, at the same time, makes it possible to carry out extrusion-molding at a markedly lower kneading temperature and with good productivity. High-concentration masterbatch pellets comprising a diacetal and a polyolefin resin can be very easily prepared. The mean mixing time of the diacetal composition for heating and kneading with molten resin is shortened, thereby remarkably improving the productivity of the resin composition. Moreover, the low-temperature molding precludes sublimation of the diacetal and suppresses the thermal decomposition, obviating the problems of stain and odor produced during molding. Furthermore, use of the composition of the invention surprisingly reduces undispersed matter in polyolefin resin compositions and remarkably improves productivity and quality.

It can be easily ascertained by observation with a polarization optical microscope under a crossed Nicol polarizer and analyzer whether the binder is uniformly dispersed on the surface and in the interior of the particles of the granular diacetal composition.

The polyolefin resin nucleating agent comprising the diacetal composition of the invention may contain, where necessary, other components such as calcium stearate or like metallic soaps conventionally employed as resin neutralizing agents, pigments, and radical inhibitors or like stabilizers.

The powdery or granulated diacetal composition of the invention or said diacetal composition and a polyolefin resin may be formed into masterbatch pellets and used for injection molding or extrusion molding. The amount of a 2–20%, preferably 5–15% masterbatch pellets to be added to the polyolefin resin is not limited and can be suitably selected, insofar as the contemplated results of the invention can be obtained. Usually, the masterbatch is added in an amount of about 0.01 to 5 wt. parts, preferably about 0.05 to 3 wt. parts, calculated as the diacetal represented by the formula (1), per 100 wt. parts of the polyolefin resin. Addition of the masterbatch in an amount within the specified range can sufficiently exhibit the effect of the invention.

Polyolefin Resin Composition

The polyolefin resin composition of the invention is prepared by blending the diacetal composition of the invention with a polyolefin resin.

As discusses above, the diacetal composition of the invention melts at a temperature lower than the melting point of the diacetal itself represented by the formula (1), which constitutes said diacetal composition. By using the diacetal composition of the invention as a nucleating agent for polyolefin resins, the polyolefin resin can be kneaded and extruded at a remarkably lower temperature, compared with the processing in which an ordinary diacetal is added to a polyolefin resin. Further, the productivity of the polyolefin resin composition is significantly increased because the mean mixing time for heating and kneading is shortened.

Polyolefin resins for use in the invention are those having a crystallinity of 5 to 100%, preferably 15 to 95%. Specific examples of such resins are polyethylene-based resins, stereoregular polypropylene-based resins, stereoregular polybutene-based resins and stereoregular ethylene-propylene-butadiene or like terpolymer resins.

Examples of polyethylene-based resins include high-density polyethylenes, medium-density polyethylenes, low-density polyethylenes, linear low-density polyethylenes and ethylene copolymers with an ethylene content of 50 wt. % or more.

Examples of polypropylene-based resins include propylene homopolymer, propylene copolymers with a propylene content of 50 wt. % or more.

Examples of polybutene-based resins include butene homopolymer and butene copolymers with a butene content of 50 wt. % or more.

The above copolymers may be random copolymers or block copolymers. The stereoregularity of these resins may be either isotactic or syndiotactic.

Comonomers which can form each of the above copolymers may be, for example, ethylene, propylene, butene, pentene, hexene, heptene, octene, nonene, decene, undecene, dodecene and like α-olefines; 1,4-endomethylenecyclohexene and like bicyclo-type monomers; methyl (meth)acrylate, ethyl (meth)acrylate and like (meth)acrylates; vinyl acetate; and maleic acid.

Known catalysts can be used for the production of the polymers without limitations. Useful catalysts include not only radical polymerization catalysts and Ziegler-Natta catalysts which are commonly employed in the art, but also a catalyst system comprising a combination of a transition metal compound (e.g., titanium halide such as titanium trichloride or titanium tetrachloride) as supported by a support mainly comprising magnesium chloride or like magnesium halide with an alkyl aluminum compound (such as triethyl aluminum or diethyl aluminum chloride), and metallocene catalysts.

The recommended melt flow rate (hereinafter referred to as "MFR", measured according to JIS K 7210-1976) of the polyolefin resins for use in the invention can be suitably selected according to the molding method to be employed and physical properties required of the molded article. The MFR of the polyolefin resin is usually 0.01 to 200 g/10 minutes, preferably 0.05 to 100 g/10 minutes. Use of a mixture of polyolefin resins different in kind or in MFR is also recommendable, insofar as the mixture has a MFR within the above specified range.

The amount of the powdery or granulated diacetal composition of the invention to be used as a nucleating agent, relative to the polyolefin resin, can be suitably selected without limitations insofar as the contemplated effects of the invention can be achieved. Usually, the diacetal composition is added in an amount of about 0.01 to 5 wt. parts, preferably about 0.05 to 3 wt. parts, calculated as the diacetal represented by the formula (1), per 100 wt. parts of the polyolefin resin. The diacetal composition, when added in an amount within the above range, can fully exhibit the effects of the invention.

The polyolefin resin composition of the invention may contain a metallic soap, where necessary. As such metallic soap to be optionally added to polyolefin resins, known are lithium salt, sodium salt, potassium salt and calcium salt of $C_{16}$–$C_{22}$ (preferably $C_{16}$–$C_{18}$) fatty acids or of 12-hydroxystearic acid. For improving transparency of the resin composition, said lithium salt and a combination of said lithium salt and said calcium salt are particularly recommendable.

The powdery or granulated diacetal composition of the invention may be used as combined with various resin additives to form a masterbatch, insofar as the contemplated effects of the present invention is not impaired. Alternatively, pellets may be prepared from ordinary proportions of the diacetal composition and additives. Specifically, for preparing the polyolefin resin composition and carrying out molding, a powdery or granulated diacetal composition already containing various resin additives may be prepared in advance and added to the polyolefin resin to obtain a resin composition, or molding is carried out while adding such a diacetal composition with various additives to the polyolefin resin, instead of individually adding the diacetal composition and other resin additives to the polyolefin resin. The working efficiency of the polyolefin resin molding is thereby remarkably improved.

Examples of such resin additives include various resin additives for polypropylene, polyethylene or polybutene listed in "The Tables of Positive Lists of Additives" edited by Japan Hygienic Olefin and Styrene Plastic Association (January, 1995). More specific examples of such additives are stabilizers [e.g., phosphorus compounds such as distearyl pentaerythritol phosphite and Irgaphos 168; metal compounds such as zinc 2-ethylhexanoate; epoxy compounds such as epoxidized soybean oil and epoxidized linseed oil; nitrogen compounds such as melamine; phosphorus compounds such as tris(nonylphenyl)phosphite; and sulfur compounds such as dialkyl ($C_{12}$–$C_{18}$) 3,3'-thiodipropionate], UV absorbers [e.g., benzophenone compounds such as 2,2'-dihydroxy-4-methoxybenzophenone and 2-hydroxy-4-n-octoxybenzophenone, and benzotriazole compounds such as 2-(2'-hydroxy-5'-methylphenyl) benzotriazole], antioxidants [e.g., phenolic compounds such as 2,6-di-tert-butyl-4-methylphenol and tetrakis[methylene-3-(3',5'-di-tert-butyl-4'-hydroxyphenyl)propionato]methane, and phosphorus compounds such as 2,4-di-tert-butylphenylphosphite], silicone oils [e.g., dimethyl polysiloxane and methyl phenyl polysiloxane], fillers [e.g., clay, kaolin, talc, hydrotalcite, mica, zeolite, perlite, diatomaceous earth, calcium carbonate, glass (beads or fibers) and wood flour], foaming agents, foaming aids, crosslinking agents, crosslinking accelerators, flame retardants, dispersants, processing aids and like resin additives.

The polyolefin resin composition of the invention can be prepared, for example, by a process comprising blending a polyolefin resin (powder or flake), a nucleating agent comprising the diacetal composition of the invention, and where necessary, the metallic soap and said other resin additives to give a powdery polyolefin resin composition, or alternatively, by a process further comprising melting and kneading said powdery polyolefin resin composition with heating (for example, at 150 to 300° C., preferably 170 to 240° C., more preferably 180° C. to 220° C., in particular at a temperature higher than the melting point of the diacetal composition), extruding the kneaded melt, cooling the extruded strands (to, for example, about 80 to 20° C., for example, by placing the strands in water), and cutting the cooled strands to thereby give pellets free of white spots due to undispersed diacetal.

Polyolefin resin composition pellets in which white spots due to undispersed diacetal are present are obtained by kneading a polyolefin resin and a diacetal composition at a temperature lower than the melting point of the diacetal composition, extruding the mixture and cooling the extruded strands.

By using any type of the above pellets, molded articles free of the white spots can be prepared by injection molding, extrusion molding or other molding methods, as will be described later.

Polyolefin Resin Molded Article

The diacetal composition of the invention melts at a temperature considerably lower than the melting point of the diacetal represented by the formula (1) as such which constitutes said diacetal composition. Accordingly, the resin composition of the invention can be molded by a conventional process at a lower temperature than the molding temperature for resin compositions comprising ordinary diacetals.

Consequently, the low-temperature molding precludes sublimation of the diacetal and suppresses thermal decomposition thereof, obviating problems of stains and odors produced during the molding process. Furthermore, undispersed material in the polyolefin resin composition is surprisingly reduced, whereby the productivity and quality are remarkably improved.

This molding method can be carried out in the molding of the resin pellets, or in the direct molding using the powdery polyolefin resin composition which is not pelletized.

The polyolefin resin composition pellets according to the present invention free of white spots due to undispersed diacetal give polyolefin resin molded articles having good transparency by a molding method such as conventional extrusion molding, injection molding, blow molding, injection-blow molding, or the like. The polyolefin resin composition pellets of the invention in which white spots due to undispersed diacetal are present also give polyolefin resin molded articles having good transparency by a similar molding method. Since the polyolefin resin composition pellets are prepared at a lower temperature, the polyolefin resin molded articles are excellent not only in transparency but also in appearance free of coloring (yellowing).

The powdery polyolefin resin compositions give polyolefin resin molded articles having good transparency by a molding method such as conventional extrusion molding, injection molding, blow molding, injection-blow molding or the like, while setting the resin temperature at a temperature which is equal to or higher than the melting point of the diacetal composition.

In either case, the transparent sheet obtained by the above extrusion molding method may be further subjected to conversion by a conventional air-pressure forming or the like to thereby give polyolefin resin formed products having good transparency.

As already described, the diacetal composition contained in the powdery polyolefin resin composition has a melting point of as low as 185 to 230° C. Accordingly, it appears that in the course of the above conventional molding process, the diacetal composition or the undispersed diacetal forming the white spots becomes. liquid at the melting temperature of the diacetal composition, and readily dissolves or disperses at molecular level in the molten resin, consequently giving a molded article with good transparency. This result is surprising and would never be achieved with use of an ordinary diacetal per se having a melting point of 255 to 280° C.

As a result, it is not always necessary to prepare polyolefin resin composition pellets which are free of white spots due to undispersed diacetal. Therefore, it is now possible to produce polyolefin resin composition pellets at a lower temperature and at a high speed, hence advantageous from the standpoint of facilities and energy saving. Furthermore, the depressed melting point of the diacetal composition which is lower than the melting point of the diacetal itself precludes sublimation of the diacetal during molding and therefore minimizes stain during the molding operation, consequently improving the molding yield, molding efficiency and productivity.

According to the present invention, molding can be carried out not only under the conditions conventionally employed, but also at a molten resin temperature which is lower than the conventional one. Thus, for example, injection molding can be carried out under the conditions: molten resin temperature=170 to 260° C., in particular 180 to 245° C., mold temperature=80 to 10° C., in particular 60 to 20° C. Extrusion molding can be carried out under the conditions: molten resin temperature=170 to 260° C., in particular 180 to 245° C., cooling temperature=80 to 10° C., in particular 60 to 20° C.

The molded articles thus obtained may be in the form of sheet, bottle, case, cap, cup, pipe and the like, and are useful as various cases, containers, and the like and also useful as automobile bumpers.

Other Applications

The diacetal composition of the invention functions not only as a polyolefin resin nucleating agent but also as a gelling agent, a viscosity controlling agent; a thixotropic agent, an anti-sagging agent, an oil-water separating agent or a coagulant for various fluids, or as a nucleating agent for resins other than polyolefin resins. The diacetal composition can therefore be used in the fields where the conventional diacetals have been employed, such as adhesives, coating compositions, perfumes and deodorants, water treating agents, solidifying agents for recovery of spilled oil, fragrances, cosmetics, materials for civil engineering or construction, lubricants, rust-preventive agents, agricultural chemicals, medicines, pseudo-pharmaceutical products, fuels, inks, adhesive pastes and the like.

EXAMPLES

Examples are given below to illustrate the present invention in detail. The following methods were employed to measure and evaluate the average value of the diameters of the particles, melting point, bulk density, flow property, uniformity, adhesion, dust suppression degree, transparency (haze) and dispersibility of the powdery or granulated diacetal composition.

Average Particle Diameter (average value of the diameters of the particles (median diameter))

The average value of diameters (median diameter) of the particles was calculated from the measurements obtained with a particle size distribution measuring apparatus with a laser diffraction/scattering (trade name "LA-910", product of Horiba, Ltd.), using distilled water as a dispersion medium. The average value of the diameters (median diameter) of the particles was hereinafter referred to simply as "average particle diameter".

Melting Point

Measurement was carried out using a differential scanning calorimeter (trade name "DSC-50", product of Shimadzu Corp.) at a heating rate of 20° C./min, and the-peak temperature due to diacetal was shown as the melting point. The sample was used in an amount of 5 mg, and 5 mg of silica gel was used as the standard sample.

Bulk Density

At a temperature of 20° C. and a humidity of 60%, a 200-ml measuring cylinder with a diameter of 38 mm containing 35 g of the sample was tapped 50 times onto a rubber mat from a height of 10 cm. Then, the bulk density was calculated from the volume of the sample in the measuring cylinder. This procedure was repeated three times to obtain an average value, which was the bulk density determined in this evaluation. The greater the bulk density, the better the flow property of the powder.

Flow Property 1 g of the sample was placed on an end portion of the bottom of a stainless steel container (5 cm in length, 10 cm in width and 5 cm in depth). The container was inclined to find the angle of repose for the sample, at which the particles at the surface of the sample started to slide. The angle of repose was used as an index of flow property. The smaller the angle of repose, the higher the flow property.

Uniformity (confirmation of uniform dispersion of binder in the particles of pulverized product)

The powdery diacetal composition obtained by pulverization was visually inspected using a polarization optical microscope under a crossed Nicol polarizer and analyzer at room temperature and while raising the temperature. The composition in which the binder is uniformly dispersed in the particle of the powdery composition was rated as ○, whereas the composition in which the binder is non-uniformly dispersed in the particle was rated as x.

Adhesion 5 g of the powdery diacetal composition was placed in a 75 ml glass bottle. The bottle was capped, shaken for 1 minute and allowed to stand. The inner wall of the bottle was checked for the adhesion of the composition. The adhesion was evaluated according to the following criteria.

⊚: no adhesion,

○: slight adhesion,

Δ: some adhesion, x: considerable adhesion.

Dust Suppression Degree 10 g of the sample was dropped, at a time,. from a height of 50 cm. Five seconds later, the degree of dust generation was visually inspected and evaluated according to the following criteria.

⊚: substantially no dust generated,

○: slight dust generated,

Δ: some dust generated, x: a large amount of dust generated.

Haze Value (transparency improving property)

The haze value was determined using a haze meter (product of Toyo Seki Seisakusho) according to JIS K6714 and JIS K6717. The smaller the value, the higher the transparency.

Dispersibility (dispersibility of the diacetal composition in polyolefin resin composition)

The number of white spots of undispersed nucleating agent in ten test pieces (5 cm×5 cm×1 mm) was counted by visual inspection to find the average number of the white spots per sheet. The smaller the number, the higher the dispersibility. The presence of 0.5 or more white spots per piece is indicative of inferiority for practical purposes.

Proportion of Binder (and additive)

The percentage by weight of the amount of binder (and also the amount of additive, if appropriate) relative to the sum of the amount of the diacetal and the amount of the binder (and the amount of an additive when additive is used) is shown.

Example 1

450 g of 1,3:2,4-O-dibenzylidene-D-sorbitol (average particle diameter: 20 μm, hereinafter referred to as "D") and 1500 ml of ethanol were placed in a 5-liter all-purpose mixer (product of Dalton) equipped with a stirrer, a condenser having a decanter, a thermometer and a gas inlet. The mixture was stirred at a rate of 50 to 60 rpm for 1 hour in a nitrogen stream under reflux. The resulting system was a swelled paste.

Subsequently, 50 g of stearic acid (acid value: 197 mg KOH/g, the same applies hereinafter) was added, followed by further 2-hour stirring under reflux.

The system was cooled to 50° C., and the solvent was gradually removed from the system under reduced pressure.

After removing most of the ethanol, the residue was granulated while drying the residue with stirring for 8 hours at 50° C./10 mm Hg. The dry granules were pulverized in a household mixer for 10 minutes to obtain a powdery diacetal composition.

Measurements were made of the average particle diameter, melting point, bulk density, flow property, uniformity, adhesion and dust suppression degree of the obtained diacetal composition. The results are shown in Table 1.

Example 2

A reactor of the same type as in Example 1 was charged with 450 g of "D" and 1500 ml of methanol. The mixture was stirred at a rate of 50 to 60 rpm in a nitrogen stream under reflux. The resulting system was a swelled paste.

A solution of 13.5 g of DL-malic acid (acid value: 807 mg KOH/g, the same applies hereinafter) in 100 ml of water was added, followed by further 2-hour stirring under reflux. The subsequent procedure was carried out in the same manner as in Example 1 to obtain a powdery diacetal composition.

Measurements were made of the average particle diameter, melting point, bulk density, flow property, uniformity, adhesion and dust suppression degree of the obtained diacetal composition. The results are shown in Table 1.

Comparative Example 1

A diacetal powder was prepared by following the procedure of Example 1 with the exception that "D" was treated without using stearic acid.

Measurements were made of the average particle diameter, melting point, bulk density, flow property, uniformity, adhesion and dust suppression degree of the diacetal powder. The results are shown in Table 1.

Example 6

150 g of ethanol was added to 400 g of the powdery diacetal composition obtained from "MD" in Example 4, giving a paste. Using an extrusion granulating machine (Eck pelletor, product of Fuji Denki Kogyo Co., Ltd.), the paste was shaped into a noodle-like solid by extrusion through a perforated disk having perforations with a diameter of 3 mm.

The resulting solid was dried at 50° C./10 mm Hg for 8 hours, and cut into cylinders of about 5 mm lenth. The obtained cylinders were pulverized in a household mixer for 1 minute, giving a powdery diacetal composition.

Measurements were made of the average particle diameter, melting point, bulk density, flow property, uniformity, adhesion and dust suppression degree of the obtained diacetal composition. The results are shown in Table 2.

TABLE 1

| | Binder | | Average | | | | | | Dust |
| --- | --- | --- | --- | --- | --- | --- | --- | --- | --- |
| | Kind | Proportion (wt. %) | particle diameter ($\mu$m) | m.p. (° C.) | Bulk density (g/cm$^3$) | Angle of Repose (degree) | Uniformity | Adhesion | suppression degree |
| Ex. 1 | Stearic acid | 10 | 25 | 217 | 0.44 | 60 | ○ | ○ | ○ |
| Ex. 2 | DL-malic acid | 2.9 | 20 | 195 | 0.30 | 65 | ○ | ○ | ○ |
| Comp. Ex.1 | — | — | 20 | 227 | 0.20 | 75< | — | X | X |

Example 3

A powdery diacetal composition was prepared by following the procedure of Example 1 with the exception of using 1,3:2,4-bis-O-(p-methylbenzylidene)-D-sorbitol (average particle diameter: 20 $\mu$m, hereinafter referred to as "MD") in place of "D".

Measurements were made of the average particle diameter, melting point, bulk density, flow property, uniformity, adhesion and dust suppression degree of the obtained diacetal composition. The results are shown in Table 2.

Example 4

A diacetal composition was prepared by following the procedure of Example 3 with the exception of using 100 g of stearic acid relative to 400 g of "MD".

Measurements were made of the average particle diameter, melting point, bulk density, flow property, uniformity, adhesion and dust suppression degree of the obtained diacetal composition. The results are shown in Table 2.

Example 5

A powdery diacetal composition was prepared by following the procedure of Example 3 with the exception of using 250 g of stearic acid relative to 250 g of "MD".

Example 7

The powdery diacetal composition obtained from "MD" in Example 3 was further pulverized and sieved, giving a powdery diacetal composition having an average particle diameter of 5 $\mu$m.

Measurements were made of the melting point, bulk density, flow property, uniformity, adhesion and dust suppression degree of the obtained diacetal composition. The results are shown in Table 2.

Example 8

A reactor of the same type as in Example 1 was charged with 273 g of D-sorbitol and 15 g of ion exchange water, giving a solution. The reactor was further charged with 360 g of p-methylbenzaldehyde, 550 g of cyclohexane, 400 g of methanol and 30 g of p-toluenesulfonic acid monohydrate. After replacing air in the reactor with nitrogen, the contents of the reactor were heated with stirring in a nitrogen atmosphere. As the methanol and water were removed in the form of vapor-liquid equilibrium mixture or an azeotropic mixture from the system, the reaction temperature rose. When the reaction temperature reached 74° C., 60 g of methanol was added. This procedure was repeated 5 times. A crude reaction product containing "MD" was thus obtained.

The crude product was cooled to room temperature, neutralized with a solution of 14 g of potassium hydroxide in 200 g of methanol, and washed five times, each time with 600 g of water at 60° C.

To the obtained slurry of diacetal swelled with the cyclohexane solvent were added 64.3 g of stearic acid and 4.0 g of L-tartaric acid (acid value: 748 mg KOH/g), followed by stirring at 70° C. for 2 hours.

After adding 600 g of warm water, the resulting mixture was heated at a temperature not higher than 100° C. to distill off cyclohexane, whereby the cyclohexane dispersion medium was replaced with water dispersion medium.

Subsequently, when the temperature reached 100° C., water was distilled off from the system while gradually reducing the pressure, and then the resulting residue was granulated while drying the residue for 10 hours at a pressure of 50 mm Hg and at a drying temperature of 80° C. to give granulated product.

The granulated product was pulverized in a household mixer for 10 minutes, giving a powdery diacetal composition containing "MD".

Measurements were made of the average particle diameter, melting point, bulk density, flow property, uniformity, adhesion and dust suppression degree. The results are shown in Table 2.

Example 9

A powdery diacetal composition containing "MD" was prepared by following the procedure of Example 3 with the exception of using behenic acid (acid value: 165 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 10

A powdery diacetal composition containing "MD" was prepared by following the procedure of Example 3 with the exception of using montanic acid wax (acid value: 140 mg KOH/g, product of Client Japan, trade name "HOE-WAX S FLAKES") in place of stearic acid and using a solvent mixture of 750 ml of ethanol and 750 ml of cyclohexane in place of 1500 ml of ethanol.

Measurements were made of the average particle diameter, melting point, bulk density, flow property, uniformity, adhesion and dust suppression degree of the obtained diacetal composition. The results are shown in Table 2.

Example 11

A powdery diacetal composition containing "MD" was prepared by following the procedure of Example 3 with the exception of using dehydroabietic acid (acid value: 186 mg/KOH/g) in place of stearic acid.

Measurements were made of the average particle diameter, melting point, bulk density, flow property, uniformity, adhesion and dust suppression degree of the obtained diacetal composition. The results are shown in Table 2.

Example 12

A powdery diacetal composition containing "MD" was prepared by following the procedure of Example 3 with the exception of using benzoic acid (acid value: 459 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 13

Granulated diacetal composition containing "MD" was prepared by following the procedure of Example 3 with the exception of using 1.35 g of L-tartaric acid (acid value: 748 mg KOH/g) in place of 50 g of stearic acid. The granulated product was not subjected to the pulverization with a household mixer.

Measurements were made of the average particle diameter, melting point, bulk density, flow property, uniformity, adhesion and dust suppression degree of the obtained granules. The results are shown in Table 2.

Example 14

A powdery diacetal composition containing "MD" was prepared by following the procedure of Example 3 with the exception of using succinic acid (acid value: 950 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 15

A powdery diacetal composition containing "MD" was prepared by following the procedure of Example 3 with the exception of using DL-malic acid in place of stearic acid.

Measurements were made of the average particle diameter, melting point, bulk density, flow property, uniformity, adhesion and dust suppression degree of the obtained diacetal composition. The results are shown in Table 2.

Example 16

A powdery diacetal composition containing "MD" was prepared by following the procedure of Example 3 with the exception of using 23.7 g of citric acid (acid value: 876 mg KOH/g, the same applies hereinafter) in place of 50 g of stearic acid.

Measurements were made of the average particle diameter, melting point, bulk density, flow property, uniformity, adhesion and dust suppression degree of the obtained diacetal composition. The results are shown in Table 2.

Example 17

A powdery diacetal composition containing "MD" was prepared by following the procedure of Example 3 with the exception of using citric acid in place of stearic acid.

Measurements were made of the average particle diameter, melting point, bulk density, flow property, uniformity, adhesion and dust suppression degree. The results are shown in Table 2.

Example 18

A powdery diacetal composition containing "MD" was prepared by following the procedure of Example 3 with the exception of using 12-hydroxystearic acid (acid value: 187 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 19

A powdery diacetal composition containing "MD" was prepared by following the procedure of Example 3 with the exception of using cholic acid (acid value: 137 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 20

A powdery diacetal composition containing "MD" was prepared by following the procedure of Example 3 with the exception of using citric acid monostearate (acid value: 245 mg KOH/g) in place of stearic acid.

Measurements were made of the average particle diameter, melting point, bulk density, flow property, uniformity, adhesion and dust suppression degree of the obtained diacetal composition. The results are shown in Table 2.

Example 21

A powdery diacetal composition containing "MD" was prepared by following the procedure of Example 3 with the exception of using citric acid distearate (acid value: 77 mg KOH/g) in place of stearic acid.

Measurements were made of the average particle diameter, melting point, bulk density, flow property, uniformity, adhesion and dust suppression degree. The results are shown in Table 2.

Example 22

A powdery diacetal composition containing "MD" was prepared by following the procedure of Example 3 with the exception of using L-glutamine (acid value: 384 mg KOH/g) in place of stearic acid.

Measurements were made of the average particle diameter, melting point, bulk density, flow property, uniformity, adhesion and dust suppression degree. The results are shown in Table 2.

Example 23

A powdery diacetal composition containing "MD" was prepared by following the procedure of Example 3 with the exception of using monostearyl pentaerythritol diphosphite (acid value: 131 mg KOH/g) in place of stearic acid.

Measurements were made of the average particle diameter, melting point, bulk density, flow property, uniformity, adhesion and dust suppression degree of the obtained diacetal composition. The results are shown in Table 2.

Comparative Example 2

A powdery solid was prepared by following the procedure of Example 3 with the exception that "MD" was treated without using stearic acid.

Measurements were made of the average particle diameter, melting point, bulk density, flow property, uniformity, adhesion and dust suppression degree of the obtained powdery solid. The results are shown in Table 2.

Comparative Example 3

A powdery solid containing "MD" was prepared by following the procedure of Example 3 with the exception of using stearyl alcohol in place of stearic acid.

Measurements were made of the average particle diameter, melting point, bulk density, flow property, uniformity, adhesion and dust suppression degree of the obtained powdery solid. The results are shown in Table 2.

Comparative Example 4

A powdery solid containing "MD" was prepared by following the procedure of Example 3 with the exception of using cholesterol in place of stearic acid.

Measurements were made of the average particle diameter, melting point, bulk density, flow property, uniformity, adhesion and dust suppression degree of the obtained powdery solid. The results are shown in Table 2.

Comparative Example 5

A powdery solid containing "MD" was prepared by following the procedure of Example 3 with the exception of using abietyl alcohol in place of stearic acid.

Measurements were made of the average particle diameter, melting point, bulk density, flow property, uniformity, adhesion and dust suppression degree of the obtained powdery solid. The results are shown in Table 2.

Comparative Example 6

A powdery solid containing "MD" was prepared by following the procedure of Example 3 with the exception of using distearylmethylamine in place of stearic acid.

Measurements were made of the average particle diameter, melting point, bulk density, flow property, uniformity, adhesion and dust suppression degree of the obtained powdery solid. The results are shown in Table 2.

Comparative Example 7

A powdery solid containing "MD" was prepared by following the procedure of Example 1 with the exception of using "MD" in place of "D", using paraffin wax in place of stearic acid, and using a solvent mixture of 750 ml of ethanol and 750 ml of cyclohexane in place of 1500 ml of ethanol.

Measurements were made of the average particle diameter, melting point, bulk density, flow property, uniformity, adhesion and dust suppression degree of the obtained powdery solid. The results are shown in Table 2.

Comparative Example 8

In a 5-liter all-purpose mixer (product of Dalton, 50 g of stearic acid was dissolved in 150 g of methanol at 60° C. To this solution was added 28 g of a 28.5% aqueous solution of sodium carbonate at 60° C., followed by 10-minute stirring. Then, 500 g of ion exchange water was gradually added. The mixture was stirred to give an emulsion of stearic acid.

450 g of "MD" was added to the emulsion. After stopping heating, the mixture was stirred, giving a white viscous milky liquid. The liquid was neutralized with dilute hydrochloric acid, filtered, washed with water and dried to obtain Measurements were made of the average particle diameter, melting point, bulk density, flow property, uniformity, adhesion and dust suppression degree of the obtained powdery solid. The results are shown in Table 2.

TABLE 2

| | Binder | | Average particle diameter ($\mu$m) | m.p. (° C.) | Bulk density (g/cm$^3$) | Angle of Repose (degree) | Uniformity | Adhesion | Dust suppression degree |
|---|---|---|---|---|---|---|---|---|---|
| | Kind | Proportion (wt. %) | | | | | | | |
| Ex.3 | Stearic acid | 10 | 25 | 240 | 0.43 | 60 | ○ | ○ | ○ |
| Ex.4 | Stearic acid | 20 | 30 | 234 | 0.56 | 55 | ○ | ○ | ◎ |
| Ex.5 | Stearic acid | 50 | 35 | 220 | 0.85 | 50 | ○ | ◎ | ◎ |
| Ex.6 | Stearic acid | 20 | 450 | 235 | 0.81 | 50 | ○ | ◎ | ◎ |
| Ex.7 | Stearic acid | 10 | 5 | 240 | 0.35 | 60 | ○ | ○ | ○ |
| Ex.8 | Stearic acid / L-tartaric acid | 9.9 / 0.62 | 25 | 200 | 0.52 | 60 | ○ | ○ | ◎ |
| Ex.9 | Behenic acid | 10 | 25 | 244 | 0.45 | 60 | ○ | ○ | ○ |
| Ex.10 | Montanic acid wax | 10 | 25 | 247 | 0.51 | 55 | ○ | ○ | ◎ |
| Ex.11 | Dehydroabietic acid | 10 | 25 | 246 | 0.43 | 60 | ○ | ○ | ○ |
| Ex.12 | Benzoic acid | 10 | 20 | 214 | 0.31 | 65 | ○ | ○ | ○ |
| Ex.13 | L-tartaric acid | 0.3 | 500 | 207 | 0.55 | 50 | ○ | ◎ | ◎ |
| Ex.14 | Succinic acid | 10 | 20 | 184 | 0.31 | 65 | ○ | ○ | ○ |
| Ex.15 | DL-malic acid | 10 | 20 | 168 | 0.32 | 65 | ○ | ○ | ○ |
| Ex.16 | Citric acid | 5 | 20 | 195 | 0.30 | 65 | ○ | ○ | ○ |
| Ex.17 | Citric acid | 10 | 20 | 166 | 0.33 | 65 | ○ | ○ | ○ |
| Ex.18 | 12-hydroxy-stearic acid | 10 | 25 | 242 | 0.43 | 60 | ○ | ○ | ○ |
| Ex.19 | Cholic acid | 10 | 30 | 244 | 0.45 | 60 | ○ | ○ | ○ |
| Ex.20 | Citric acid monostearate | 10 | 25 | 230 | 0.48 | 60 | ○ | ○ | ○ |
| Ex.21 | Citric acid distearate | 10 | 25 | 249 | 0.53 | 60 | ○ | ○ | ◎ |
| Ex.22 | L-glutamine | 10 | 25 | 207 | 0.35 | 60 | ○ | ○ | ○ |
| Ex.23 | Monostearyl pentaerythritol diphosphite | 10 | 25 | 224 | 0.41 | 60 | ○ | ○ | ○ |
| Comp. Ex.2 | — | — | 20 | 262 | 0.20 | 75< | — | X | X |
| Comp. Ex.3 | Stearyl alcohol | 10 | 20 | 261 | 0.29 | 65 | ○ | Δ | Δ |
| Comp. Ex.4 | Cholesterol | 10 | 20 | 260 | 0.29 | 70 | ○ | Δ | Δ |
| Comp. Ex.5 | Abietyl alcohol | 10 | 20 | 261 | 0.29 | 70 | ○ | Δ | Δ |
| Comp. Ex.6 | Distearyl methyl amine | 10 | 20 | 261 | 0.29 | 70 | ○ | Δ | Δ |
| Comp. Ex.7 | Paraffin wax | 10 | 30 | 260 | 0.60 | 55 | ○ | ◎ | ◎ |
| Comp. Ex.8 | Stearic acid (surface-coat) | 10 | 25 | 260 | 0.39 | 60 | X | ○ | ○ |
| Comp. Ex.9 | Stearic acid (surface-coat) | 20 | 25 | 255 | 0.49 | 60 | X | ○ | ○ | a dry powder. The obtained dry powder was pulverized in a household mixer for 10 minutes to give a powdery solid. Measurements were made of the average particle diameter, melting point, flow property, uniformity, adhesion and dust suppression degree of the powdery solid. The results are shown in Table 2.

Comparative Example 9

A powdery solid was prepared by following the procedure of Comparative Example 8 with the exception of changing the amount of ion exchange water from 500 g to 375 g and changing the amount of 1,3:2,4-bis-O-(p-methylbenzylidene)-D-sorbitol ("MD") from 450 g to 200 g.

Example 24

A powdery diacetal composition was prepared by following the procedure of Example 1 with the exception of using 1,3:2,4-bis-O-(3,4-dimethylbenzylidene)-D-sorbitol (average particle diameter: 20 $\mu$m, hereinafter referred to as "DMD") in place of "D".

Measurements were made of the average particle diameter, melting point, bulk density, flow property, uniformity, adhesion and dust suppression degree of the obtained diacetal composition. The results are shown in Table 3.

Example 25

A powdery diacetal composition mainly comprising "DMD" was prepared by following the procedure of Example 24 with the exception of using 13.5 g of citric acid in place of 50 g of stearic acid.

Measurements were made of the average particle diameter, melting point, bulk density, flow property, uniformity, adhesion and dust suppression degree of the obtained diacetal composition. The results are shown in Table 3.

Example 26

A diacetal composition was prepared by following the procedure of Example 13 with the exception of using "DMD" in place of "MD".

Measurements were made of the average particle diameter, melting point, bulk density, flow property, uniformity, adhesion and dust suppression degree of the obtained diacetal composition. The results are shown in Table 3.

Comparative Example 10

A powder was prepared by following the procedure of Example 24 with the exception that "DMD was treated without using stearic acid.

Measurements were made of the average particle diameter, melting point, bulk density, flow property, uniformity, adhesion and dust suppression degree of the obtained powder. The results are shown in Table 3.

Example 29

The reactor of the same type as in Example 1 was charged with 450 g of "MD" and 1500 ml of methanol. The mixture was stirred at a rate of 50 to 60 rpm for 1 hour in a nitrogen atmosphere under reflux. The resulting system was a swelled paste.

To the system was added a solution of 4.5 g of L-tartaric acid in 20 ml of water, and 50 g of hardened castor oil, followed by 2-hour stirring under reflux. The system was cooled to 50° C., and the solvent was gradually removed from the system under reduced pressure. After most of the ethanol was removed, the system was dried with stirring at a reduced pressure of 10 mm Hg for 8 hours, giving a dry powder.

The dry powder was pulverized in a household mixer for 10 minutes to give a powdery diacetal composition mainly comprising "MD".

Measurements were made of the average particle diameter, melting point, bulk density, flow property, uniformity, adhesion and dust suppression degree of the obtained powdery diacetal composition. The results are shown in Table 4.

Example 30

A reactor of the same type as in Example 1 was charged with 273 g of D-sorbitol and 15 g of ion exchange water,

TABLE 3

| | Binder | | Average | | | | | | |
| --- | --- | --- | --- | --- | --- | --- | --- | --- | --- |
| | Kind | Proportion (wt. %) | particle diameter ($\mu$m) | m.p. (° C.) | Bulk density (g/cm$^3$) | Angle of Repose (degree) | Uniformity | Adhesion | Dust suppression degree |
| Ex.24 | Stearic acid | 10 | 25 | 249 | 0.43 | 60 | ○ | ○ | ○ |
| Ex.25 | Citric acid | 2.9 | 20 | 210 | 0.30 | 65 | ○ | ○ | ○ |
| Ex.26 | L-tartaric acid | 0.3 | 470 | 205 | 0.60 | 50 | ○ | ◎ | ◎ |
| Comp. Ex.10 | — | — | 20 | 276 | 0.20 | 75< | — | X | X |

Example 27

A powdery diacetal composition was prepared by following the procedure of Example 1 with the exception of adding 50 g of stearic acid and 23.5 g of an antistatic agent, i.e., glycerine monostearate (acid value: 5 mg KOH/g, the same applies hereinafter) to 400 g of "MD".

Measurements were made of the average particle diameter, melting point, bulk density, flow property, uniformity, adhesion and dust suppression degree of the obtained diacetal composition. The results are shown in Table 4.

Example 28

A powdery diacetal composition was prepared by following the procedure of Example 1 with the exception of adding 30 g of an aqueous solution of 47.1 g of stearic acid, 1.2 g of L-tartaric acid and 2.0 g of sodium butylnaphthalenesulfonate to 400 g of "MD".

Measurements were made of the average particle diameter, melting point, bulk density, flow property, giving a solution. To the solution was added 360 g of p-methylbenzaldehyde, 550 g of cyclohexane, 400 g of methanol and 30 g of p-toluenesulfonic acid monohydrate. After replacing air in the reactor with nitrogen, the contents of the reactor were heated with stirring in a nitrogen atmosphere. As the methanol and water were removed in the form of a vapor-liquid equilibrium mixture or an azeotropic mixture from the system, the reaction temperature rose. When the reaction temperature reached 74° C., 60 g of methanol was added. This procedure was repeated 15 times. The system was then cooled to room temperature, neutralized with a solution of 14 g of potassium hydroxide in 200 g of methanol, and washed seven times, each time with 600 g of water at 60° C.

To the resulting diacetal swelled with the cyclohexane solvent were added 5.8 g of sodium dodecylbenzenesulfonate and 2.4 g of L-tartaric acid (acid value: 748 mg KOH/g), and the mixture was stirred at 70° C. for 2 hours.

600 g of warm water was added to the system, and the system was heated to 100° C. to distill off cyclohexane, whereby the cyclohexane dispersion medium was replaced with an aqueous dispersion medium.

After the reaction temperature reached 100° C., water was distilled off from the system while gradually reducing the pressure, and then at a drying temperature of 80° C./50 mmHg the diacetal composition was granulated while drying it for 10 hours to give dry granulated product.

Measurements were made of the average particle diameter, melting point, bulk density, flow property, uniformity, adhesion and dust suppression degree of the obtained dry granulated product. The results are shown in Table 4.

Example 31

A reactor of the same type as in Example 1 was charged with 273 g of D-sorbitol and 15 g of ion exchange water, giving a solution. To the solution was added 402 g of 3,4-dimethylbenzaldehyde, 550 g of cyclohexane, 400 g of methanol and 30 g of p-toluenesulfonic acid monohydrate. After replacing air in the reactor with nitrogen, the contents of the reactor were heated with stirring in a nitrogen atmosphere. As the methanol and water were removed in the form of a vapor-liquid equilibrium mixture or an azeotropic mixture from the system, the reaction temperature rose. When the reaction temperature reached 74° C., 60 g of methanol was added. This procedure was repeated 10 times. The system was then cooled to room temperature, neutralized with a solution of 14 g of potassium hydroxide in 200 g of methanol, and washed seven times, each time with 600 g of water at 60° C.

To the resulting diacetal swelled with the cyclohexane solvent were added 6.2 g of sodium dodecylbenzene-sulfonate and 2.5 g of L-tartaric acid (acid value: 748 mg KOH/g), and the mixture was stirred at 70° C. for 2 hours. Then, 600 g of warm water was added to the system, and the system was heated to 100° C. to distill off cyclohexane, whereby the cyclohexane dispersion medium was replaced with water dispersion medium.

After the reaction system reached 100° C., water was distilled off from the system while gradually reducing the pressure, and then at a drying temperature of 80° C./50 mmHg, the diacetal composition was granulated while drying for 10 hours to give granulated product.

Measurements were made of the average particle diameter, melting point, bulk density, flow property, uniformity, adhesion and dust suppression degree of the obtained granulated product. The results are shown in Table 4.

Example 32

Granulated product was prepared by following the procedure of Example 31 with the exception of using 3.1 g of sodium dodecylbenzenesulfonate, 3.1 g of L-tartaric acid and 62.1 g of behenic acid in place of 6.2 g of sodium dodecylbenzenesulfonate and 2.5 g of L-tartaric acid.

Measurements were made of the average particle diameter, melting point, bulk density, flow property, uniformity, adhesion and dust suppression degree of the obtained granulated product containing "DMD". The results are shown in Table 4.

Example 33

Granulated product was prepared by following the procedure of Example 30 with the exception of using 5.8 g of sodium dodecylbenzenesulfonate in place of 5.8 g of sodium dodecylbenzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 34

Granulated product was prepared by following the procedure of Example 30 with the exception of using 17.4 g of sodium dodecylbenzenesulfonate in place of 5.8 g of sodium dodecylbenzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 35

Granulated product was prepared by following the procedure of Example 30 with the exception of using 5.8 g of sodium α-olefin ($C_{18}$) sulfonate in place of 5.8 g of sodium dodecylbenzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 36

Granulated product was prepared by following the procedure of Example 30 with the exception of using 17.4 g of sodium lauryl sulfate in place of 5.8 g of sodium dodecyl-benzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 37

Granulated product was prepared by following the procedure of Example 30 with the exception of using 17.4 g of aluminum distearate in place of 5.8 g of sodium dodecyl-benzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 38

Granulated product was prepared by following the procedure of Example 30 with the exception of using 62.1 g of aluminum distearate in place of 5.8 g of sodium dodecyl-benzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 39

Granulated product was prepared by following the procedure of Example 30 with the exception of using 17.4 g of aluminum monostearate in place of 5.8 g of sodium dodecylbenzenesulfonate and 2.4 g of L-tartaric acid.

Measurements were made of the average particle diameter, melting point, bulk density, flow property, uniformity, adhesion and dust suppression degree of the obtained granulated product containing "MD". The results are shown in Table 4.

Example 40

Granulated product was prepared by following the procedure of Example 34 with the exception of using 5.8 g of sodium laurylsulfate and 11.6 g of aluminum distearate in place of 17.4 g of sodium dodecylbenzenesulfonate.

Measurements were made of the average particle diameter, melting point, bulk density, flow property, uniformity, adhesion and dust suppression degree of the obtained granulated product containing "MD". The results are shown in Table 4.

Example 41

Dryblended with a Henschel mixer were 100 wt. parts of an isotactic random polypropylene resin (hereinafter referred to as "r-PP") with an ethylene content of 3.0 wt. %; 0.2 wt. part (calculated as a pure diacetal content) of the powdery diacetal composition obtained in Example 1 as a polyolefin nucleating composition; and 0.05 wt. part of calcium stearate; and 0.05 wt. part of tetrakis[methylene-3-(3,5-di-tert-butyl-4-hydroxyphenyl)propionato]methane (trade name "Irganox 1010", product of Ciba Geigy).

The dryblend was melted, kneaded and extrusion-molded using a single screw extruder at 220° C. The obtained strands were cooled with water and cut into pellets.

The pellets were injection-molded at a resin temperature of 220° C. and a mold temperature of 40° C. to prepare a test piece with a thickness of 1 mm. The haze value and the number of spots due to undispersed nucleating composition of the test piece were determined. The results are shown in Table 5.

Examples 42 to 70

A test piece was prepared by following the procedure of Example 41 and using each of the compositions obtained in Examples 2 to 29 and 31 as a nucleating composition for r-PP.

Table 5 shows the kind of the diacetal composition employed in each Example, temperature for extrusion in preparing the pellets and the injection molding temperature in preparing the test pieces, and the haze value and the number of white spots formed from undispersed nucleating composition determined with respect to the test pieces.

TABLE 4

| | diacetal | Binder and additives Kind | Proportion (wt. %) | Average particle diameter (μm) | m.p. (° C.) | Bulk density (g/cm³) | Angle of repose (degree) | Uniformity | Adhesion | Dust suppression degree |
|---|---|---|---|---|---|---|---|---|---|---|
| Ex.27 | MD | Stearic acid | 10.6 | 25 | 238 | 0.52 | 55 | ○ | ◎ | ◎ |
| | | Glycerine monostearate | 5 | | | | | | | |
| Ex.28 | MD | Stearic acid | 10.5 | 25 | 220 | 0.45 | 60 | ○ | ◎ | ◎ |
| | | L-tartaric acid | 0.27 | | | | | | | |
| | | Sodium butylnaphtharenesulfonate | 0.44 | | | | | | | |
| Ex.29 | MD | L-tartaric acid | 0.89 | 25 | 190 | 0.51 | 55 | ○ | ◎ | ◎ |
| | | Hardened castor oil | 9.9 | | | | | | | |
| Ex.30 | MD | L-tartaric acid | 0.41 | 3000 | 190 | 0.85 | 40 | ○ | ◎ | ◎ |
| | | Sodium dodecylbenzenesulfonate | 0.99 | | | | | | | |
| Ex.31 | DMD | L-tartaric acid | 0.40 | 210 | 196 | 0.50 | 50 | ○ | ◎ | ◎ |
| | | Sodium dodecylbenzenesulfonate | 0.98 | | | | | | | |
| Ex.32 | DMD | Sodium dodecylbenzenesulfonate | 0.45 | 600 | 196 | 0.85 | 40 | ○ | ◎ | ◎ |
| | | L-tartaric acid | 0.45 | | | | | | | |
| | | Behenic acid | 9.0 | | | | | | | |
| Ex.33 | MD | Sodium dodecylbenzenesulfonate | 0.99 | 300 | 248 | 0.41 | 40 | ○ | ◎ | ◎ |
| Ex.34 | MD | Sodium dodecylbenzenesulfonate | 2.9 | 280 | 233 | 0.40 | 40 | ○ | ◎ | ◎ |
| Ex.35 | MD | Sodium α-olefin sulfonate | 0.99 | 280 | 251 | 0.40 | 40 | ○ | ◎ | ◎ |
| Ex.36 | MD | Sodium laurylsulfate | 2.9 | 300 | 204 | 0.40 | 40 | ○ | ◎ | ◎ |
| Ex.37 | MD | Aluminum distearate | 2.9 | 290 | 226 | 0.35 | 45 | ○ | ◎ | ○ |
| Ex.38 | MD | Aluminum distearate | 9.7 | 290 | 205 | 0.50 | 40 | ○ | ◎ | ◎ |
| Ex.39 | MD | Aluminum monostearate | 2.9 | 290 | 239 | 0.35 | 40 | ○ | ◎ | ○ |
| Ex.40 | MD | Sodium laurylsulfate | 1.0 | 290 | 214 | 0.45 | 40 | ○ | ◎ | ◎ |
| | | Aluminum distearate | 2.0 | | | | | | | |

Comparative Examples 11 to 20

A test piece was prepared by following the procedure of Example 41 and using each of the compositions obtained in Comparative Examples 1 to 10 as a nucleating composition for r-PP.

Table 5 shows the kind of the diacetal composition employed in each Comparative Example, temperature for extrusion in preparing the pellets and the injection molding temperature in preparing the test piece, and the measured haze value and the number of white spots formed from undispersed nucleating composition with respect to the test pieces.

Comparative Example 21

A test piece of r-PP was prepared by following the procedure of Example 41 with the exception that no nucleating diacetal was used.

The measured haze value of the test piece and the number of white spots formed from undispersed nucleating agent found therein is shown in Table 5.

TABLE 5

Nucleating effect on r-PP

| | diacetal composition | | Temperature for extrusion and injection (° C.) | Haze value | Undispersed spot number (per sheet) |
|---|---|---|---|---|---|
| | Prepared in | Diacetal | | | |
| Ex.41 | Example 1 | D | 220 | 17 | 0 |
| Ex.42 | Example 2 | D | 220 | 17 | 0 |
| Ex.43 | Example 3 | MD | 240 | 11 | 0 |
| Ex.44 | Example 4 | MD | 240 | 11 | 0 |
| Ex.45 | Example 5 | MD | 240 | 11 | 0 |
| Ex.46 | Example 6 | MD | 240 | 11 | 0.1 |
| Ex.47 | Example 7 | MD | 240 | 11 | 0 |
| Ex.48 | Example 8 | MD | 240 | 11 | 0 |
| Ex.49 | Example 9 | MD | 240 | 11 | 0.1 |
| Ex.50 | Example 10 | MD | 240 | 11 | 0.2 |
| Ex.51 | Example 11 | MD | 240 | 11 | 0 |
| Ex.52 | Example 12 | MD | 240 | 11 | 0 |
| Ex.53 | Example 13 | MD | 220 | 12 | 0 |
| Ex.54 | Example 14 | MD | 220 | 11 | 0 |
| Ex.55 | Example 15 | MD | 220 | 11 | 0 |
| Ex.56 | Example 16 | MD | 220 | 11 | 0 |
| Ex.57 | Example 17 | MD | 220 | 11 | 0 |
| Ex.56 | Example 18 | MD | 240 | 11 | 0.1 |
| Ex.59 | Example 19 | MD | 240 | 11 | 0.1 |
| Ex.60 | Example 20 | MD | 240 | 11 | 0 |
| Ex.61 | Example 21 | MD | 240 | 11 | 0.2 |
| Ex.62 | Example 22 | MD | 220 | 11 | 0 |
| Ex.63 | Example 23 | MD | 240 | 12 | 0 |
| Ex.64 | Example 24 | DMD | 240 | 13 | 0.2 |
| Ex.65 | Example 25 | DMD | 220 | 12 | 0 |
| Ex.66 | Example 26 | DMD | 220 | 13 | 0 |
| Ex.67 | Example 27 | MD | 240 | 10 | 0 |
| Ex.68 | Example 28 | MD | 240 | 10 | 0 |
| Ex.69 | Example 29 | MD | 220 | 11 | 0 |
| Ex.70 | Example 31 | DMD | 220 | 12 | 0 |
| Comp.Ex.11 | Comp.Ex.1 | D | 220 | 20 | 1.8 |
| Comp.Ex.12 | Comp.Ex.2 | MD | 240 | 12 | 2.6 |
| Comp.Ex.13 | Comp.Ex.3 | MD | 240 | 12 | 2.4 |
| Comp.Ex.14 | Comp.Ex.4 | MD | 240 | 12 | 2.3 |
| Comp.Ex.15 | Comp.Ex.5 | MD | 240 | 12 | 2.3 |
| Comp.Ex.16 | Comp.Ex.6 | MD | 240 | 12 | 2.3 |
| Comp.Ex.17 | Comp.Ex.7 | MD | 240 | 12 | 2.0 |
| Comp.Ex.19 | Comp.Ex.8 | MD | 240 | 11 | 1.2 |
| Comp.Ex.19 | Comp.Ex.9 | MD | 240 | 11 | 1.0 |
| Comp.Ex.20 | Comp.Ex.10 | DMD | 240 | 14 | 2.6 |
| Comp.Ex.21 | — | Not added | 240 | 70 | 0 |

Example 71

Dryblended with a Henschel mixer were 100 wt. parts of a linear low-density polyethylene resin (density=0.2926 g/cm$^3$, MFR=20 g/10 min., hereinafter referred to as "LLDPE"), and the powdery diacetal composition obtained in Example 1 in an amount of 0.2 wt. part calculated as a pure diacetal content.

The dryblend was melted, kneaded and extrusion-molded using a single screw extruder at 200° C. The obtained strands were cooled with water and cut into pellets.

The pellets were injection-molded at a resin temperature of 200° C. and a mold temperature of 300° C. to prepare a test piece with a thickness of 1 mm.

The haze value and the number of the white spots formed from undispersed nucleating composition were determined with respect to the test pieces. The results are shown in Table 6.

Examples 72 to 74

A test piece was prepared by following the procedure of Example 71 and using each of the nucleating compositions obtained in Examples 2, 30 and 32 for LLDPE.

Table 6 shows the kind of the nucleating composition, extrusion temperature in preparing the pellets and injection molding temperature in preparing the test piece employed in each Example, and the haze value and the number of the white spots formed from undispersed nucleating composition determined with respect to the test pieces.

Comparative Example 22

A test piece consisting of LLDPE alone was prepared by following the procedure of Example 71.

Table 6 shows the haze value and white spot number formed from undispersed nucleating composition determined with respect to the test piece containing no diacetal composition.

TABLE 6

Nucleating effect on LLDPE

| | diacetal composition | | Temperature for extrusion and injection (° C.) | Haze value | Undispersed spot number per sheet |
|---|---|---|---|---|---|
| | Prepared in | diacetal | | | |
| Ex. 71 | Example 1 | D | 200 | 24 | 0.3 |
| Ex. 72 | Example 2 | D | 210 | 25 | 0 |
| Ex. 73 | Example 30 | MD | 210 | 20 | 0 |
| Ex. 74 | Example 32 | DMD | 210 | 24 | 0 |
| Comp. Ex. 22 | — | Not added | 200 | 54 | 0 |

INDUSTRIAL APPLICABILITY

According to the present invention, the melting point of the diacetals is remarkably depressed. As a result, the diacetal composition of the invention dissolves in molten resins or various fluids at a higher rate, thereby enabling the diacetal to dissolve at a low temperature or within a shorter period of time. Further, undissolved matter in the resulting product is greatly reduced, whereby the quality and productivity are significantly improved.

Moreover, the increase in the bulk density of the diacetal composition due to the binder effect leads to a significant improvement in the working environment by suppression of dust, and facilitates the transfer of the composition because of the improved powder properties such as improved flow property and reduced adhesion.

Moreover, the composition of the invention can be used as a polyolefin resin nucleating agent amenable to low-temperature molding. It improves the moldability, suppresses sublimation and decomposition of the diacetal and prevent the coloration of the resin composition.

What is claimed is:

1. A granular or powdery diacetal composition comprising:

(a) at least one diacetal represented by the formula (1)

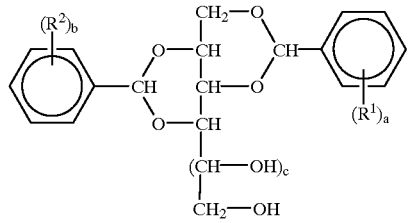

(1)

wherein $R^1$ and $R^2$ are the same or different and each represent a hydrogen atom, a $C_1$–$C_4$ alkyl group, a $C_1$–$C_4$ alkoxy group, a $C_1$–$C_4$ alkoxycarbonyl group or a halogen atom; a and b each represent an integer of 1 to 5; c is 0 or 1; when a is 2, the two $R^1$'s taken together with the benzene ring to which they are linked may form a tetralin ring; and when b is 2, the two $R^2$'s taken together with the benzene ring to which they are linked may form a tetralin ring; and (b) at least one binder selected from the group consisting of neutral or weakly acidic monovalent organic acids, neutral or weakly acidic polyvalent organic acids, partial salts of neutral or weakly acidic polyvalent organic acids, salts of a sulfuric acid ester, sulfonic acid salts, salts of a phosphoric acid ester, phosphoric acid esters, phosphorous acid esters and aluminum salts of a neutral or weakly acidic monovalent organic acid, the binder being uniformly dispersed in the particles of the granular or powdery diacetal composition such that the binder is uniformly distributed among the fibrous diacetal crystals constituting the granular or powdery diacetal composition.

2. A powdery diacetal composition comprising:

(a) at least one diacetal represented by the formula (1)

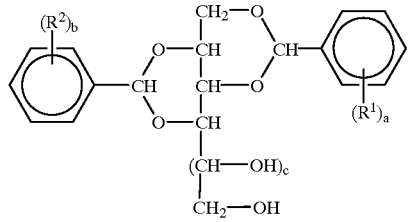

(1)

wherein $R^1$ and $R^2$ are the same or different and each represent a hydrogen atom, a $C_1$–$C_4$ alkyl group, a $C_1$–$C_4$ alkoxy group, a $C_1$–$C_4$ alkoxycarbonyl group or a halogen atom, a and b each represent an integer of 1 to 5, and c is 0 or 1, and (b) a binder comprising at least one organic acid as an essential component, the binder being uniformly dispersed in the diacetal such that the binder is uniformly distributed among the fibrous diacetal crystals constituting the granular or powder diacetal composition, and the composition having an average particle diameter of 3 to 500 μm.

3. A granular or powdery diacetal composition according to claim 1 wherein the binder is selected from the group consisting of monocarboxylic acids, polycarboxylic acids, partial salts of polycarboxylic acids, esters of phosphoric acid and at least one member selected from the group consisting of $C_1$–$C_{30}$ monohydric aliphatic alcohols and $C_2$–$C_{30}$ polyhydric aliphatic alcohols, esters of phosphorous acid and at least one member selected from the group consisting of $C_1$–$C_{30}$ monohydric aliphatic alcohols and $C_2$–$C_{30}$ polyhydric aliphatic alcohols, esters of phosphoric acid and at least one member selected from the group consisting of $C_6$–$C_{30}$ monohydric aromatic alcohols and $C_6$–$C_{30}$ polyhydric aromatic alcohols, esters of phosphorous acid and at least one member selected from the group consisting of $C_6$–$C_{30}$ monohydric aromatic alcohols and $C_6$–$C_{30}$ polyhydric aromatic alcohols, taurine, salts of sulfuric acid ester, sulfonic acid salts, salts of phosphoric acid ester and mono-, di- and tri($C_6$–$C_{30}$ fatty acid) aluminum salts, each of which may have, in the molecule, at least one bond or functional group selected from the group consisting of an ether bond, an ester bond, a thioether bond, an amide bond, a halogen atom, amino group, hydroxyl groups, a heterocyclic group and carbonyl group.

4. A granular or powdery diacetal composition according to claim 1 which is obtainable by:

(i) preparing a slurry containing the diacetal represented by the formula (1) swelled with a solvent, (ii) uniformly mixing the slurry with the binder, (iii) (a) removing the solvent from the obtained uniform mixture to give a dry product, or (b) granulating the obtained uniform mixture while removing the solvent from the mixture, or (c) sifting or pulverizing the dry product obtained in step (a) or the granulated product obtained in step (b), or (d) granulating or sifting the pulverized product obtained in step (c).

5. A granular or powdery diacetal composition according to claim 1 wherein the binder depresses the melting point of the diacetal by 7° C. or more, when the composition contains 10 wt. parts of the binder as uniformly dispersed in 90 wt. parts of the diacetal represented by the formula (1), the binder being selected from the group consisting of monocarboxylic acids, polycarboxylic acids, partial salts of polycarboxylic acids, esters of phosphoric acid with at least one member selected from the group consisting of $C_1$–$C_{30}$ monohydric aliphatic alcohols and $C_2$–$C_{30}$ polyhydric aliphatic alcohols, esters of phosphorous acid with at least one member selected from the group consisting of $C_1$–$C_{30}$ monohydric aliphatic alcohols and $C_2$–$C_{30}$ polyhydric aliphatic alcohols, esters of phosphoric acid with at least one member selected from the group consisting of $C_6$–$C_{30}$ monohydric aromatic alcohols and $C_6$–$C_{30}$ polyhydric aromatic alcohols, esters of phosphorous acid with at least one member selected from the group consisting of $C_6$–$C_{30}$ monohydric aromatic alcohols and $C_6$–$C_{30}$ polyhydric aromatic alcohols, taurine, salts of sulfuric acid ester, sulfonic acid salts, salts of phosphoric acid ester and mono-, di- and tri($C_6$–$C_{30}$ fatty acid) aluminum salts, each of which may have, in the molecule, at least one bond or functional group selected from the group consisting of an ether bond, an ester bond, a thioether bond, amide bond, a halogen atom, amino group, hydroxyl group, a heterocyclic group and carbonyl group.

6. The granular or powdery diacetal composition according to claim 1, wherein the binder is at least one member selected from the group consisting of monocarboxylic acids, polycarboxylic acids, partial salts of polycarboxylic acids, sulfonic acid salts, salts of sulfuric acid ester, salts of phosphoric acid ester and mono-, di- and tri($C_6$–$C_{30}$ fatty acid) aluminum salts, each of which may have, in the molecule, at least one bond or functional group selected from the group consisting of an ether bond, an ester bond, a thioether bond, amide bond, a halogen atom, amino group, hydroxyl group, a heterocyclic group and carbonyl group.

7. The granular or powdery diacetal composition according to claim 1 wherein the binder is a monocarboxylic or polycarboxylic acid with an acid value of 60 to 1200 mg KOH/g, which may have, in the molecule, at least one bond or functional group selected from the group consisting of an ether bond, an ester bond, a thioether bond, amide bond, a halogen atom, amino group, hydroxyl group, a heterocyclic group and carbonyl group.

8. The granular or powdery diacetal composition according to claim 1 wherein the binder is at least one member selected from the group consisting of aliphatic monocarboxylic acids having 80 or less carbon atoms, aliphatic polycarboxylic acids having 80 or less carbon atoms and their alkyl ($C_1$–$C_{22}$) partial esters, aromatic monocarboxylic acid having 80 or less carbon atoms, aromatic polycarboxylic acids having 80 or less carbon atoms and their alkyl ($C_1$–$C_{22}$) partial esters, halogen atom-containing carboxylic acids having 80 or less carbon atoms, amino group-containing carboxylic acids having 80 or less carbon atoms, amide bond-containing carboxylic acids having 80 or less carbon atoms, hydroxyl group-containing carboxylic acids having 80 or less carbon atoms, resin acids, carbonyl group-containing carboxylic acids having 80 or less carbon atoms, ether bond-containing carboxylic acids having 80 or less carbon atoms, ester bond-containing carboxylic acids having 80 or less carbon atoms, amide bond- and amino group-containing carboxylic acids having 80 or less carbon atoms, amide bond- and hydroxyl group-containing carboxylic acids having 80 or less carbon atoms, heterocyclic ring-containing carboxylic acids having 80 or less carbon atoms, and thioether bond-containing carboxylic acids having 80 or less carbon atoms.

9. The granular or powdery diacetal composition according to claim 1 wherein the binder is at least one member selected from the group consisting of $C_3$–$C_{35}$ aliphatic monocarboxylic acids, $C_4$–$C_{30}$ aliphatic polycarboxylic acids and their alkyl ($C_1$–$C_{22}$) partial esters, $C_7$–$C_{35}$ aromatic monocarboxylic acids, $C_8$–$C_{30}$ aromatic polycarboxylic acids and their alkyl ($C_1$–$C_{22}$) partial esters, halogen atom-containing $C_4$–$C_{35}$ carboxylic acids, amino group-containing $C_4$–$C_{35}$ carboxylic acids, hydroxyl group-containing $C_4$–$C_{35}$ carboxylic acids, resin acids, carbonyl group-containing $C_4$–$C_{35}$ carboxylic acids, ether bond-containing $C_4$–$C_{35}$ carboxylic acids, ester bond-containing $C_4$–$C_{35}$ carboxylic acids, amide bond- and amino group-containing $C_4$–$C_{35}$ carboxylic acids, amide bond- and hydroxyl group-containing $C_4$–$C_{35}$ carboxylic acids, heterocyclic ring-containing $C_4$–$C_{35}$ carboxylic acids and thioether bond-containing $C_4$–$C_{35}$ carboxylic acids.

10. The granular or powdery diacetal composition according to claim 1 wherein the binder is at least one member selected from the group consisting of:

(a) $C_8$–$C_{30}$ aliphatic monocarboxylic acids, (b) $c_3$–$C_{18}$ aliphatic dicarboxylic acids, $C_6$–$C_{30}$ aliphatic tricarboxylic acids, and $C_8$–$C_{30}$ aliphatic tetracarboxylic acids, (c) $C_7$–$C_{15}$ aromatic monocarboxylic acids, (d) $C_8$–$C_{20}$ aromatic di-, tri- and tetra-carboxylic acids, (e) $C_3$–$C_{20}$ carboxylic acids containing 1 to 3 halogen atoms, (f) $C_5$–$C_{12}$ mono- and dicarboxylic acids containing 1 to 3 amino groups, (g) mono-, di- and tri($C_6$–$C_{30}$ fatty acid) aluminum salts, (h) $C_4$–$C_{24}$ mono-, di-, tri- and tetracarboxylic acids containing 1 to 5 hydroxyl groups, (i) resin acids, (j) $C_4$–$C_{18}$ mono- and dicarboxylic acids containing 1 to 3 carbonyl groups, (k) $C_8$–$C_{15}$ mono- and dicarboxylic acids having 1 to 2 ether bonds, (l) $C_5$–$C_{26}$ mono- and dicarboxylic acids having 1 to 2 ester bonds, (m) (m-1) alkali metal salts, ammonium salts and alkaline earth metal salts of $C_6$–$C_{30}$ alkanesulfonic acids, of $C_6$–$C_{30}$ alkenesulfonic acids, of ($C_1$–$C_{22}$ alkyl) benzenesulfonic acids and of ($C_1$–$C_{14}$ alkyl) naphthalenesulfonic acids; and (m-2) salts of sulfuric acid ester of a $C_6$–$C_{30}$ saturated or unsaturated aliphatic alcohol; salts of sulfuric acid ester of a $C_6$–$C_{30}$ saturated or unsaturated aliphatic alcohol to which 1 to 10 moles of ethylene oxide has been added; salts of sulfosuccinic acid diester; salts of α-sulfo-fatty acid and salts of α-sulfo-fatty acid ester.

11. The granular or powdery diacetal composition according to claim 1 wherein the binder is at least one member selected from the group consisting of:

(a') lauric acid, tridecanoic acid, myristic acid, pentadecanoic acid, palmitic acid, heptadecanoic acid, stearic acid, isostearic acid, eicosanoic acid, behenic acid, docosahexanoic acid, montanic acid, benzilic acid, sorbic acid, oleic acid, linoleic acid, linolenic acid, (b') succinic acid, glutaric acid, malonic acid, adipic acid, suberic acid, azelaic acid, sebacic acid, dodecanedioic acid, itaconic acid, tricarballylic acid, 1,2,3,4-butanetetracarboxylic acid, citrazinic acid, 1,2,3,4-cyclopentanetetracarboxylic acid, 1,4-cyclohexanedicarboxylic acid, 1,2-cyclohexanedicarboxylic acid, 4,4'-dicyclohexyldicarboxylic acid, cyclohexanetetracarboxylic acid, (c') benzoic acid, p-methylbenzoic acid, p-ethylbenzoic acid, p-n-propylbenzoic acid, cuminic acid, p-tert-butylbenzoic acid, p-isobutylbenzoic acid, p-phenylbenzoic acid, 3,5-dimethylbenzoic acid, 1-naphthoic acid, 2-naphthoic acid, tetralinmonocarboxylic acid, (d') o-phthalic acid, m-phthalic acid, p-phthalic acid, trimellitic acid, trimesic acid, pyromellitic acid, diphenic acid, biphenyldicarboxylic acid, biphenyltetracarboxylic acid, naphthalenedicarboxylic acid, diphenylsulfonetetracarboxylic acid, diphenylethertetracarboxylic acid, diphenylmethanetetracarboxylic acid, diphenylpropanetetracarboxylic acid, ethylene glycol-4,4'-bistrimellitic acid ditrimellitate, (e') chloropropionic acid, bromopropionic acid, o-chlorobenzoic acid, m-chlorobenzoic acid, p-chlorobenzoic acid, 4-chloro-3-nitrobenzoic acid, (f') L-glutamine, (g') aluminum mono- or dipelargonate, aluminum mono- or dilaurate, aluminum mono- or dimyristate, aluminum mono- or distearate, and, aluminum mono- or dioleate, (h') tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid and α,β-dihydroxyhexahydrophthalic acid, (i') dehydroabietic acid, abietic acid, dihydroabietic acid, neoabietic acid, tetrahydroabietic acid, (j') levulinic acid, pyruvic acid, o-benzoylbenzoic acid, (k') 4-methoxycyclohexanecarboxylic acid, 4-ethoxycyclohexanecarboxylic acid, p-methoxybenzoic acid, p-ethoxybenzoic acid, p-phenoxybenzoic acid, (l') acetylcitric acid, stearoylcitric acid, acetylricinoleic acid, stearoyllactic acid, citric acid monostearyl ester, adipic acid mono-2-ethylhexyl ester, adipic acid monooctyl ester, and (m') sodium and potassium salts of $C_{18}$ alkane- or alkenesulfonic acid, sodium dodecylbenzenesulfonate, sodium dodecylsulfate, sodium dodecylethersulfate (i.e., sodium salt of sulfuric acid ester with dodecyl alcohol to which 1 mole of ethylene oxide has been added), sodium dioctyl sulfosuccinate and sodium methyl α-sulfostearate.

12. The granular or powdery diacetal composition according to claim 1 wherein the binder is at least one member of (h) a $C_4$–$C_{24}$ mono-, di-, tri- and tetracarboxylic acids having 1 to 5 hydroxyl groups.

13. The granular or powdery diacetal composition according to claim 1 wherein the binder is at least one member selected from the group consisting of tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid and α,β-dihydroxyhexahydrophthalic acid.

14. The granular or powdery diacetal composition according to claim 1 wherein the binder is at least one member selected from the group consisting of:

(h-a) tartaric acid, lactic acid, malic acid, citric acid, succinic acid and α,β-dihydroxyhexahydrophthalic acid, and (m) (m-1) alkali metal salts, ammonium salts and alkaline earth metal salts of $C_6$–$C_{30}$ alkanesulfonic acids, of $C_6$–$C_{30}$ alkenesulfonic acids, of ($C_1$–$C_{22}$ alkyl) benzenesulfonic acids, and of ($C_1$–$C_{14}$ alkyl) naphthalenesulfonic acids, and (m-2) salts of sulfuric acid esters of $C_6$–$C_{30}$ saturated and unsaturated aliphatic alcohols, salts of sulfuric acid esters of $C_6$–$C_{30}$ saturated and unsaturated aliphatic alcohols to which 1 to 10 moles of ethylene oxide has been added, salts of sulfo-succinic acid diester, salts of α-sulfo-fatty acid and salts of α-sulfo-fatty acid ester.

15. The granular or powdery diacetal composition according to claim 1 which comprises, as the binder, at least one member selected from the group consisting of:

(h-a) tartaric acid, malic acid, citric acid, succinic acid and α,β-dihydroxyhexahydrophthalic acid, (m) (m-1) alkaline earth metal salts, ammonium salts and alkali metal salts of $C_6$–$C_{30}$ alkanesulfonic acids, of $C_6$–$C_{30}$ alkenesulfonic acids, of ($C_1$–$C_{22}$ alkyl) benzenesulfonic acids, and of ($C_1$–$C_{14}$ alkyl) naphthalenesulfonic acids and (m-2) salts of sulfuric acid esters of $C_6$–$C_{30}$ saturated and unsaturated aliphatic alcohols, salts of sulfuric acid esters of $C_6$–$C_{30}$ saturated and unsaturated aliphatic alcohols to which 1 to 10 moles of ethylene oxide has been added, salts of sulfo-succinic acid diester, salts of α-sulfo-fatty acid and salts of α-sulfo-fatty acid ester, (a) $C_8$–$C_{30}$ aliphatic monocarboxylic acids, and (g) mono-, di- and tri($C_6$–$C_{30}$ fatty acid) aluminum salts, and which further comprises a hardened oil as a lubricant.

16. The granular or powdery diacetal composition according to claim 1 which comprises, as the binder, at least one member selected from the group consisting of:

(h-a) tartaric acid, malic acid, citric acid, succinic acid and α,β-dihydroxyhexahydrophthalic acid, (m) (m-1) alkali metal salts, ammonium salts and alkaline earth metal salts of $C_6$–$C_{30}$ alkanesulfonic acids, of $C_6$–$C_{30}$ alkenesulfonic acids, of ($C_1$–$C_{22}$ alkyl) benzenesulfonic acids, and of ($C_1$–$C_{14}$ alkyl) naphthalenesulfonic acids and (m-2) salts of sulfuric acid esters of $C_6$–$C_{30}$ saturated and unsaturated aliphatic alcohols, salts of sulfuric acid esters of $C_6$–$C_{30}$ saturated and unsaturated aliphatic alcohols to which 1 to 10 moles of ethylene oxide has been added, salts of sulfo-succinic acid diester, salts of α-sulfo-fatty acid and salts of α-sulfo-fatty acid ester, and (a) $C_8$–$C_{30}$ aliphatic monocarboxylic acids, and which further comprises a hardened oil as a lubricant.

17. The granular or powdery diacetal composition according to claim 1 which comprises, as the binder, at least one member selected from the group consisting of:

(m) (m-1) alkali metal salts, ammonium salts and alkaline earth metal salts of $C_6$–$C_{30}$ alkanesulfonic acids, of $C_6$–$C_{30}$ alkenesulfonic acids, of ($C_1$–$C_{22}$ alkyl) benzenesulfonic acids, and of ($C_1$–$C_{14}$ alkyl) naphthalenesulfonic acids and (m-2) salts of sulfuric acid esters of $C_6$–$C_{30}$ saturated and unsaturated aliphatic alcohols, salts of sulfuric acid esters of $C_6$–$C_{30}$ saturated and unsaturated aliphatic alcohols to which 1 to 10 moles of ethylene oxide has been added, salts of sulfo-succinic acid diester, salts of α-sulfo-fatty acid and salts of α-sulfo-fatty acid ester, and (a) $C_8$–$C_{30}$ aliphatic monocarboxylic acids, and which further comprises a hardened oil as a lubricant.

18. The granular or powdery diacetal composition according to claim 1 which comprises, as the binder, at least one member selected from the group consisting of:

(g) mono-, di- and tri($C_6$–$C_{30}$ fatty acid) aluminum salts, (a) $C_8$–$C_{30}$ aliphatic monocarboxylic acids (m) (m-1) alkali metal salts, ammonium salts and alkali metal salts of $C_6$–$C_{30}$ alkanesulfonic acids, of $C_6$–$C_{30}$ alkenesulfonic acids, of ($C_1$–$C_{22}$ alkyl)benzenesulfonic acids, and of ($C_1$–$C_{14}$ alkyl)naphthalenesulfonic acids and (m-2) salts of sulfuric acid esters of $C_6$–$C_{30}$ saturated and unsaturated aliphatic alcohols, salts of sulfuric acid esters of $C_6$–$C_{30}$ saturated and unsaturated aliphatic alcohols to which 1 to 10 moles of ethylene oxide has been added, salts of sulfo-succinic acid diester, salts of α-sulfo-fatty acid and salts of α-sulfo-fatty acid ester, and which further comprises a hardened oil as a lubricant.

19. The granular or powdery diacetal composition according to claim 1 wherein the binder is present in an amount of 0.01 to 100 wt. parts, per 100 wt. parts of the diacetal represented by the formula (1).

20. The granular or powdery diacetal composition according to claim 10 wherein the binder is present in an amount of 0.01 to 8 wt. parts, per 100 wt. parts of the diacetal represented by the formula (1).

21. The granular or powdery diacetal composition according to claim 1 which has an average particle diameter of 3 to 2,000 µm.

22. The granular or powdery diacetal composition according to claim 1 wherein the particles are in the form of cylinders having a sectional diameter of 0.2 to 5 mm and a length of 0.2 to 15 mm, or in the form of granules or flakes having a diameter of 0.2 to 5 mm.

23. The granular or powdery diacetal composition according to claim 1 which has a bulk density of 0.2 to 1.1 g/cm$^3$.

24. The granular or powdery diacetal composition according to claim 1 which has a melting point that is lower than that of the diacetal represented by the formula (1) contained in the diacetal composition by at least 20° C.

25. The granular or powdery diacetal composition according to claim 1 which has a melting point that is lower than that of the diacetal represented by the formula (1) contained in the diacetal composition by at least 40° C.

26. The granular or powdery diacetal composition according to claim 1 which further comprises at least one member selected from the group consisting of an antistatic agent, a neutralizing agent or stabilizer and a lubricant.

27. The granular or powdery diacetal composition according to claim 26 wherein the antistatic agent is at least one member selected from the group consisting of glycerine fatty acid ($C_8$–$C_{22}$) mono-, di- and triesters, N,N-bis(2-hydroxyethyl)alkyl($C_8$–$C_{22}$) amines, polyoxyethylene (4–50 moles) alkyl ($C_{12}$–$C_{22}$) ethers, polyoxyethylene (4–50 moles) alkyl($C_7$–$C_{22}$)phenyl ethers and pentaerythritol fatty acid ($C_8$–$C_{22}$) esters.

28. The granular or powdery diacetal composition according to claim 26 wherein the neutralizing agent or stabilizer is at least one member selected from the group consisting of calcium stearate, lithium stearate, potassium stearate, sodium stearate, tetrakis[methylene-3-(3',5'-di-t-butyl-4'-hydroxyphenyl)propionato]methane, tris(2,4-di-t-butylphenyl)phosphite and distearyl 3,3'-thiodipropionate.

29. The granular or powdery diacetal composition according to claim 26 wherein the lubricant is at least one hardened oil.

30. The composition according to claim 1, wherein the granular or powdery diacetal composition comprises, in addition to the 1,3:2,4-diacetal represented by the formula (1), at least one member selected from the group consisting of monoacetals, triacetals and diacetal isomers, formed as by-products in the condensation reaction of a pentahydric or hexahydric alcohol with an optionally substituted benzaldehyde, the total amount of the monoacetals, triacetals and diacetal isomers being 0.05 to 10 wt. % based on the total amount of the acetals (total amount of the 1,3:2,4-diacetal, monoacetals, triacetals and diacetal isomers).

31. A process for preparing a granular or powdery diacetal composition comprising:
(I) at least one diacetal represented by the formula (1)

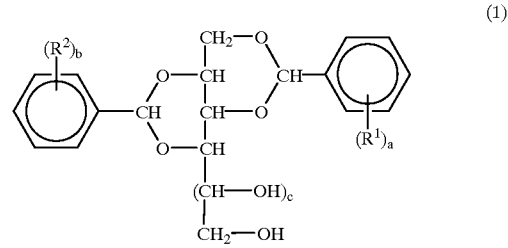

wherein $R^1$ and $R^2$ are the same or different and each represent a hydrogen atom, a $C_1$–$C_4$ alkyl group, a $C_1$–$C_4$ alkoxy group, a $C_1$–$C_4$ alkoxycarbonyl group or a halogen atom; a and b each represent an integer of 1 to 5; c is 0 or 1; when a is 2, the two $R^1$'s taken together with the benzene ring to which they are attached may form a tetralin ring; and when b is 2, the two $R^2$'s taken together with the benzene ring to which they are attached may form a tetralin ring, and (II) at least one binder selected from the group consisting of neutral or weakly acidic monovalent organic acids, neutral or weakly acidic polyvalent organic acids, partial salts of neutral or weakly acidic polyvalent organic acids, salts of sulfuric acid ester, sulfonic acid salts, salts of phosphoric acid ester, phosphoric acid esters, phosphorous acid esters and aluminum salts of a neutral or weakly acidic monovalent organic acid, the binder being uniformly dispersed in the interior of the particles of the granular or powdery diacetal composition such that the binder is uniformly distributed among the fibrous diacetal crystals constituting the granular or powdery diacetal composition, the process comprising the steps of:
(i) preparing a slurry comprising the diacetal represented by the formula (1) in a solvent, wherein the diacetal is present as swelled with the solvent,
(ii) uniformly mixing the slurry with the binder,
(iii) (a) removing the solvent from the uniform mixture obtained in step (ii) to obtain a dry product, or
(b) granulating the uniform mixture while removing the solvent from the mixture, or
(c) sifting or pulverizing the dry product obtained in step (a) or the granulated product obtained in step (b), or
(d) sifting or granulating the pulverized product obtained in step (c).

32. The process according to claim 31 wherein the slurry containing the swelled diacetal is prepared by swelling a powder of the diacetal with the organic solvent capable of swelling the powder of the diacetal.

33. The process according to claim 31 wherein the organic solvent is a polar organic solvent, or an aromatic hydrocarbon solvent, or a mixture of (a) at least one member selected from the group consisting of a polar organic solvent and an aromatic hydrocarbon and (b) at least one member selected from the group consisting of an aliphatic hydrocarbon and an alicyclic hydrocarbon, said polar organic solvent being at least one member selected from the group consisting of $C_1$–$C_{18}$ aliphatic alcohols; $C_6$–$C_{18}$ alicyclic alcohols; furfuryl alcohol; cyclic ethers; ketones; aliphatic amines having about 3 to 6 carbon atoms; acetonitrile; glycol ethers; dimethylformamide, dimethylacetamide, dimethylsulfoxide and N-methylpyrrolidone.

34. The process according to claim 31 wherein the slurry containing the swelled diacetal represented by the formula (1) is a reaction mixture obtained by subjecting corresponding sorbitol or xylitol and a substituted or unsubstituted benzaldehyde to condensation reaction in an organic solvent, or a mixture obtained by neutralizing said reaction mixture or washing said reaction mixture with water.

35. The process according to claim 31 wherein the slurry containing the swelled diacetal represented by the formula (1) is a reaction mixture obtained by subjecting corresponding sorbitol or xylitol and substituted or unsubstituted benzaldehyde to condensation reaction in water in the presence of an acid catalyst, or a aqueous slurry obtained by neutralizing said reaction mixture or washing said reaction mixture with water.

36. A polyolefin resin nucleating agent comprising the granular or powdery diacetal composition according to claim 1.

37. A polyolefin resin nucleating agent according to claim 36 wherein the diacetal composition further contains at least one member selected from the group consisting of an antistatic agent, neutralizing agent or stabilizer and a lubricant.

38. A powdery polyolefin resin composition obtainable by blending (i) a powdery or flaky polyolefin resin and a powder or granules of the nucleating agent according to claim 36 or (ii) a powdery or flaky polyolefin resin, a powder or granules of the nucleating agent according to claim 36 or 37 and at least one of additives for polyolefin resins.

39. A polyolefin resin composition obtainable by blending (i) a powdery or flaky polyolefin resin and the nucleating agent according to claim 36 or 37, or (ii) a powdery or flaky polyolefin resin, the nucleating agent according to claim 36 and at least one of additives for polyolefin resins; melting and kneading the obtained powdery composition with heating; extruding the composition; cooling the extruded strands; and cutting the obtained strands into pellets.

40. A process for preparing a polyolefin resin composition comprising blending (i) a powdery or flaky polyolefin resin and the nucleating agent according to claim 36, or (ii) a powdery or flaky polyolefin resin, a powder of the nucleating agent according to claim 36 or 37 and at least one of additives for polyolefin resins; melting and kneading the obtained powdery composition with heating at a temperature which is not lower than or lower than the melting point of the diacetal composition; extruding the composition; cooling the extruded strands; and cutting the obtained strands.

41. A process for producing a polyolefin resin molded article comprising the steps of molding the polyolefin resin composition according to claim 38 by injection molding, injection-blow molding, blow molding or extrusion molding, or subjecting a sheet obtained by said extrusion molding to air-pressure forming, the molded article containing a minimal amount of undispersed nucleating agent.

42. A polyolefin resin molded article obtainable by molding the polyolefin resin composition according to claim 38 by injection molding, injection-blow molding, blow molding or extrusion molding, or subjecting a sheet obtained by said extrusion molding to air-pressure forming.

43. The composition according to claim 42 wherein the binder is at least one member selected from the group consisting of tartaric acid, lactic acid, malic acid, citric acid, gluconic acid, pantothenic acid, 12-hydroxystearic acid, mandelic acid, cholic acid, β-oxynaphthoic acid, ricinoleic acid, quinic acid, shikimic acid, salicylic acid, protocatechunic acid and coumaric acid, and gallic acid.

* * * * *

UNITED STATES PATENT AND TRADEMARK OFFICE
CERTIFICATE OF CORRECTION

PATENT NO.    : 6,245,843 B1
DATED         : June 12, 2001
INVENTOR(S)   : Kobayashi et al.

It is certified that error appears in the above-identified patent and that said Letters Patent is hereby corrected as shown below:

<u>Title page,</u>
Item [30], change:

"Oct. 3, 1997 (JP)................10-287924" to
-- Oct. 3, 1997 (JP)................9-287924 --.

Signed and Sealed this

Nineteenth Day of March, 2002

Attest:

Attesting Officer

JAMES E. ROGAN
Director of the United States Patent and Trademark Office